United States Patent
Tsuboi et al.

(10) Patent No.: US 12,105,043 B2
(45) Date of Patent: Oct. 1, 2024

(54) GAS SENSOR AND GAS SENSOR CARTRIDGE

(71) Applicant: FUJITSU LIMITED, Kawasaki (JP)

(72) Inventors: Osamu Tsuboi, Kawasaki (JP); Michio Ushigome, Atsugi (JP); Satoru Momose, Atsugi (JP); Yoshio Kikuchi, Ninomiya (JP)

(73) Assignee: FUJITSU LIMITED, Kawasaki (JP)

( * ) Notice: Subject to any disclaimer, the term of this patent is extended or adjusted under 35 U.S.C. 154(b) by 925 days.

(21) Appl. No.: 17/115,841

(22) Filed: Dec. 9, 2020

(65) Prior Publication Data

US 2021/0088465 A1  Mar. 25, 2021

Related U.S. Application Data

(63) Continuation of application No. PCT/JP2018/024694, filed on Jun. 28, 2018.

(51) Int. Cl.
*G01N 27/12* (2006.01)
*A61L 2/10* (2006.01)
(Continued)

(52) U.S. Cl.
CPC .............. *G01N 27/125* (2013.01); *A61L 2/10* (2013.01); *A61L 2/26* (2013.01); *G01N 33/0027* (2013.01);
(Continued)

(58) Field of Classification Search
CPC .... G01N 27/125; G01N 33/0027; A61L 2/10; A61L 2/26; A61L 2202/11; A61L 2202/24
See application file for complete search history.

(56) References Cited

U.S. PATENT DOCUMENTS

| | | |
|---|---|---|
| 2017/0299536 A1 | 10/2017 | Tsuboi et al. |
| 2019/0183418 A1 | 6/2019 | Hunt et al. |
| 2020/0158653 A1* | 5/2020 | Truex ............... G08B 21/12 |

FOREIGN PATENT DOCUMENTS

| | | |
|---|---|---|
| JP | H08-114566 A | 5/1996 |
| JP | 2000-055853 A | 2/2000 |

(Continued)

OTHER PUBLICATIONS

K.V. Rajani et al., "Deposition of Earth-abundant P-type CuBr Films with High Hole Conductivity and Realization of P—CuBr/n-Si Heterojunction Solar Cell", Materials Letters 111(2013), pp. 63-66, Elsevier Journal Homepage: www.elsevier.com/locate/matlet (Total 63 pages).

(Continued)

*Primary Examiner* — Jill A Warden
*Assistant Examiner* — Alex Ramirez
(74) *Attorney, Agent, or Firm* — Fujitsu Intellectual Property Center

(57) ABSTRACT

A gas sensor includes: a gas sensor cartridge; and a gas sensor body to which the gas sensor cartridge, which includes: a case that has an intake port and an exhaust port and serves as a gas sensor chamber; a gas sensor device provided inside the case; an external connection terminal provided at the case and connected to the gas sensor device; a first sealing member that seals the intake port such that the intake port is opened when the gas sensor cartridge is attached to the gas sensor body; and a second sealing member that seals the exhaust port such that the exhaust port is opened when the gas sensor cartridge is attached to the gas sensor body, is detachably attached.

15 Claims, 38 Drawing Sheets

(51) Int. Cl.
*A61L 2/26* (2006.01)
*G01N 33/00* (2006.01)

(52) U.S. Cl.
CPC ........ *A61L 2202/11* (2013.01); *A61L 2202/24* (2013.01)

(56) References Cited

FOREIGN PATENT DOCUMENTS

| | | | |
|---|---|---|---|
| JP | 2007-248210 A | | 9/2007 |
| JP | 2007-271628 A | | 10/2007 |
| JP | 2012-167952 A | | 9/2012 |
| JP | 2015094616 A | * | 5/2015 |
| JP | 2017-191036 A | | 10/2017 |
| WO | 2017/193176 A1 | | 11/2017 |

OTHER PUBLICATIONS

Henri Mozzanega et al, "NH3 Oxidation Over UV-Irradiated TiO2 at Room Temperature", The Journal of Physical Chemistry, vol. 83, No. 17, 1979, pp. 2251-2255 (Total 5 pages).

Osamu Tsuboi et al., "Mobile Sensor that Quickly and Selectively Measures Ammonia Gas Components in Breath", Fujitsu Sci. Tech. J., vol. 53, No. 2, pp. 38-43, Feb. 2017 (Total 38 pages).

Shohei Onishi et al., "Ammonia Metabolism During Exercise", Bulletin of Keio Gijuku University Health Management Center and Keio Gijuku University Sports Medical Research Center, vol. 8, No. 1, pp. 9-14, 1989 (Total 7 pages).

International Search Report and Written Opinion of the International Searching Authority (Form PCT/ISA/210, 220, and 237), mailed in connection with PCT/JP2018/024694 and mailed Sep. 25, 2018 (Total 10 pages).

* cited by examiner

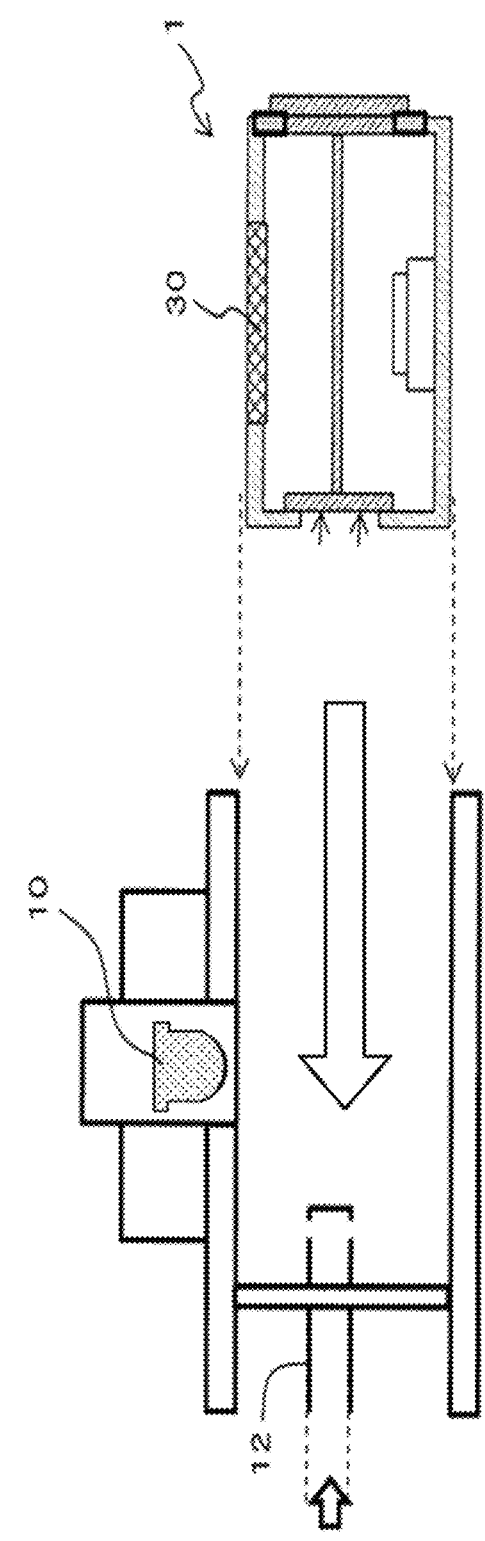
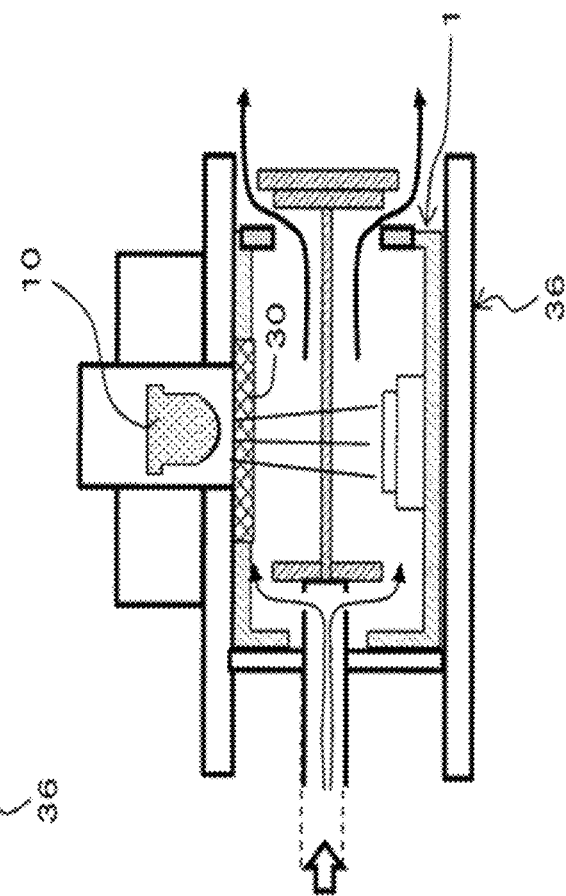
FIG. 8A
FIG. 8B

GAS SENSOR AND GAS SENSOR CARTRIDGE

CROSS-REFERENCE TO RELATED APPLICATION

This application is a continuation application of International Application PCT/JP2018/024694 filed on Jun. 28, 2018 and designated the U.S., the entire contents of which are incorporated herein by reference.

FIELD

The embodiments discussed herein are related to a gas sensor and a gas sensor cartridge.

BACKGROUND

In a gas sensor in related art, a sensor unit is detachable from a sensor body and can be replaced with a new one in order to cope with, for example, failure, deterioration, life end, and the like of the sensor unit including a sensor device.

Japanese Laid-open Patent Publication No. 2012-167952, Japanese Laid-open Patent Publication No. 2007-248210, and Japanese Laid-open Patent Publication No. 8-114566 are disclosed as related art.

SUMMARY

According to an aspect of the embodiments, a gas sensor includes: a gas sensor cartridge; and a gas sensor body to which the gas sensor cartridge, which includes: a case that has an intake port and an exhaust port and serves as a gas sensor chamber; a gas sensor device provided inside the case; an external connection terminal provided at the case and connected to the gas sensor device; a first sealing member that seals the intake port such that the intake port is opened when the gas sensor cartridge is attached to the gas sensor body; and a second sealing member that seals the exhaust port such that the exhaust port is opened when the gas sensor cartridge is attached to the gas sensor body, is detachably attached.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 3A is the cross-sectional view horizontally taken along a crosswise direction in FIG. 1, and FIG. 3B is the cross-sectional view vertically taken along the crosswise direction in FIG. 1;

FIG. 6A is the cross-sectional view horizontally taken along a crosswise direction in FIG. 4, and FIG. 6B is the cross-sectional view vertically taken along the crosswise direction in FIG. 4;

FIG. 7A illustrates a state in which an intake port and an exhaust port are closed by a first sealing member and a second sealing member, and FIG. 7B illustrates a state in which the first sealing member and the second sealing member are moved and the intake port and the exhaust port are opened;

FIGS. 8A and 8B are schematic cross-sectional views illustrating the configuration of the gas sensor cartridge and a configuration of a gas sensor socket provided in a gas sensor body according to the present embodiment, FIG. 8A illustrates a state before the gas sensor cartridge is inserted into the gas sensor socket, and FIG. 8B illustrates a state after the gas sensor cartridge is inserted into the gas sensor socket;

DESCRIPTION OF EMBODIMENTS

However, there is a case where characteristics of a sensor device fluctuate depending on, for example, storage conditions or use conditions because the sensor device included in replacement components is open to outside air.

An object of an embodiment is to reduce fluctuations in the characteristics of the sensor device.

Hereinafter, a gas sensor and a gas sensor cartridge according to the present embodiment will be described by using the drawings with reference to FIGS. 1 to 38.

The gas sensor according to the present embodiment is used as a gas sensor (gas sensor for medical/health care) that identifies components of a biogas (for example, a breath, a body odor, urine, fart, or feces) released from, for example, a body or excrement of a human, an animal, or the like.

Note that the gas sensor is also referred to as a gas concentration analyzer, a gas concentration measurement device, a gas concentration measurement system, a gas sensor system, or a measurement device.

Figure 2:
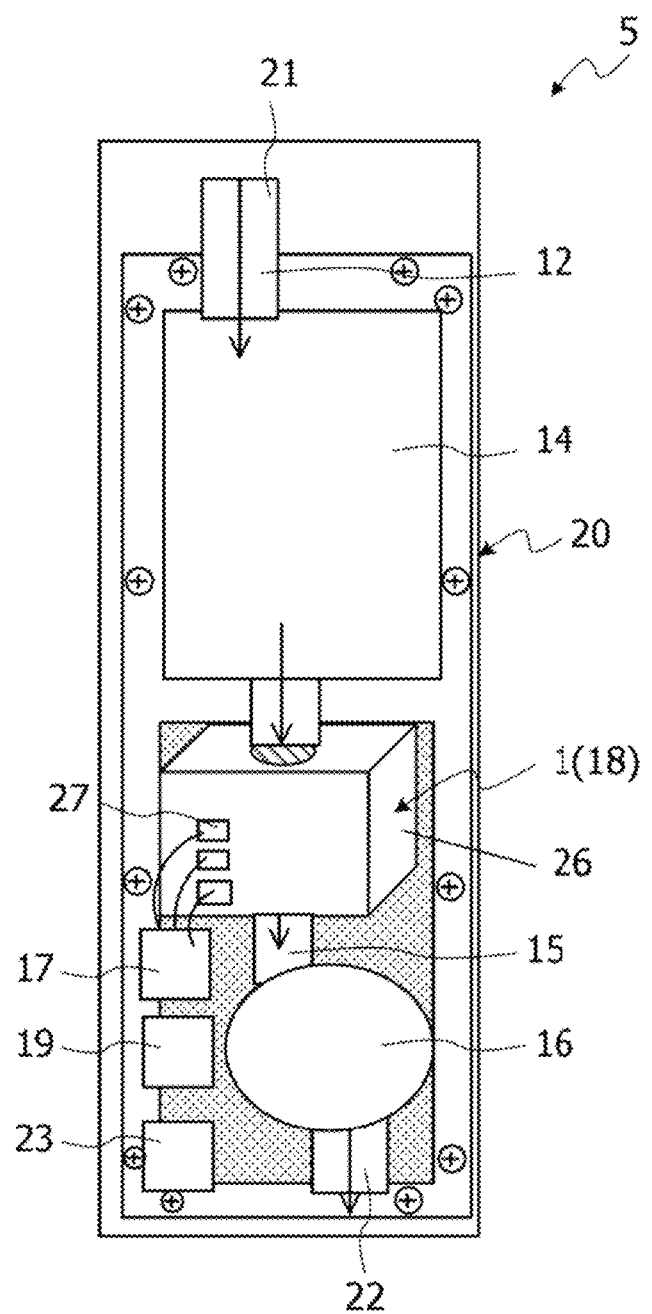
FIG. 2 is a schematic diagram illustrating a configuration of a gas sensor according to the present embodiment.

In the present embodiment, as illustrated in FIG. 2, a gas sensor 5 includes a gas sensor cartridge 1 and a gas sensor body 20 to which the gas sensor cartridge 1 is detachably attached.

Here, the gas sensor body 20 includes, for example: an inlet 21; a gas supply-side pipe 12 connected to the inlet 21; a filter 14 provided in the gas supply-side pipe 12; an outlet 22; an exhaust-side pipe 15 connected to the outlet 22; a pump 16 (or a fan) provided in the exhaust-side pipe 15; a control unit 17 such as a microcomputer and the like; a communication unit (transmission unit) 19 such as a wireless unit and the like; and a power source 23 such as a battery and the like.

Note that the gas sensor body 20 may include a display unit that displays set values, detection values, measurement values, and the like.

Figure 1:
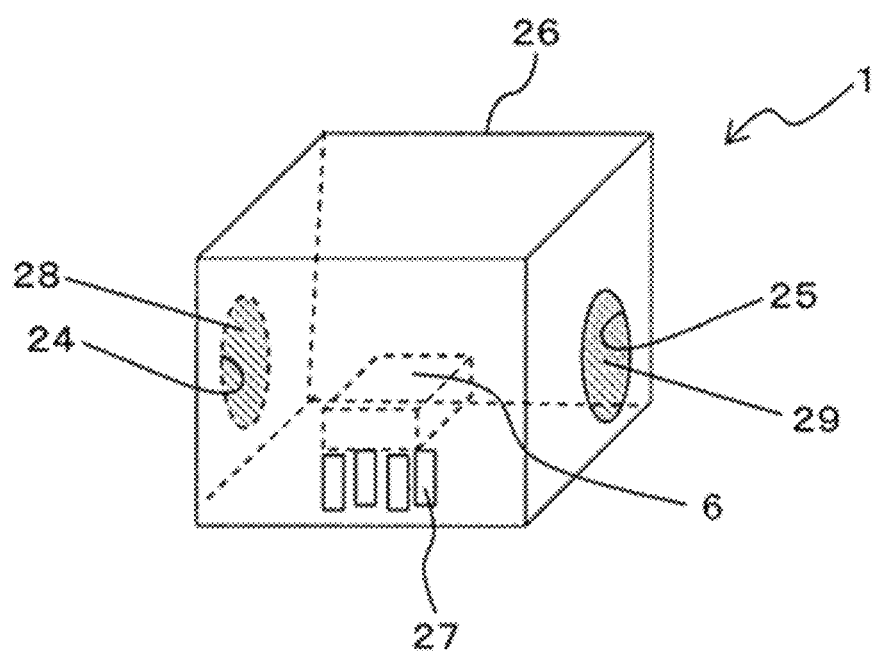
FIG. 1 is a schematic perspective view illustrating a configuration of a gas sensor cartridge according to a present embodiment.

As illustrated in FIG. 1, the gas sensor cartridge 1 includes: a case 26 that includes an intake port 24 and an exhaust port 25 and serves as a gas sensor chamber 18; a gas sensor device 6 provided inside the case 26; and an external connection terminal 27 provided at the case 26 and connected to the gas sensor device 6.

Note that the gas sensor chamber 18 is also referred to as a gas measurement chamber or a sensor chamber. Furthermore, the case 26 may include, for example, metal, an inert resin, and the like. Furthermore, the gas sensor cartridge 1 is also referred to as a replacement cartridge. Furthermore, the case 26 is also referred to as a housing. Furthermore, the external connection terminal 27 is also referred to as an external lead terminal or an electrode.

Figure 33:
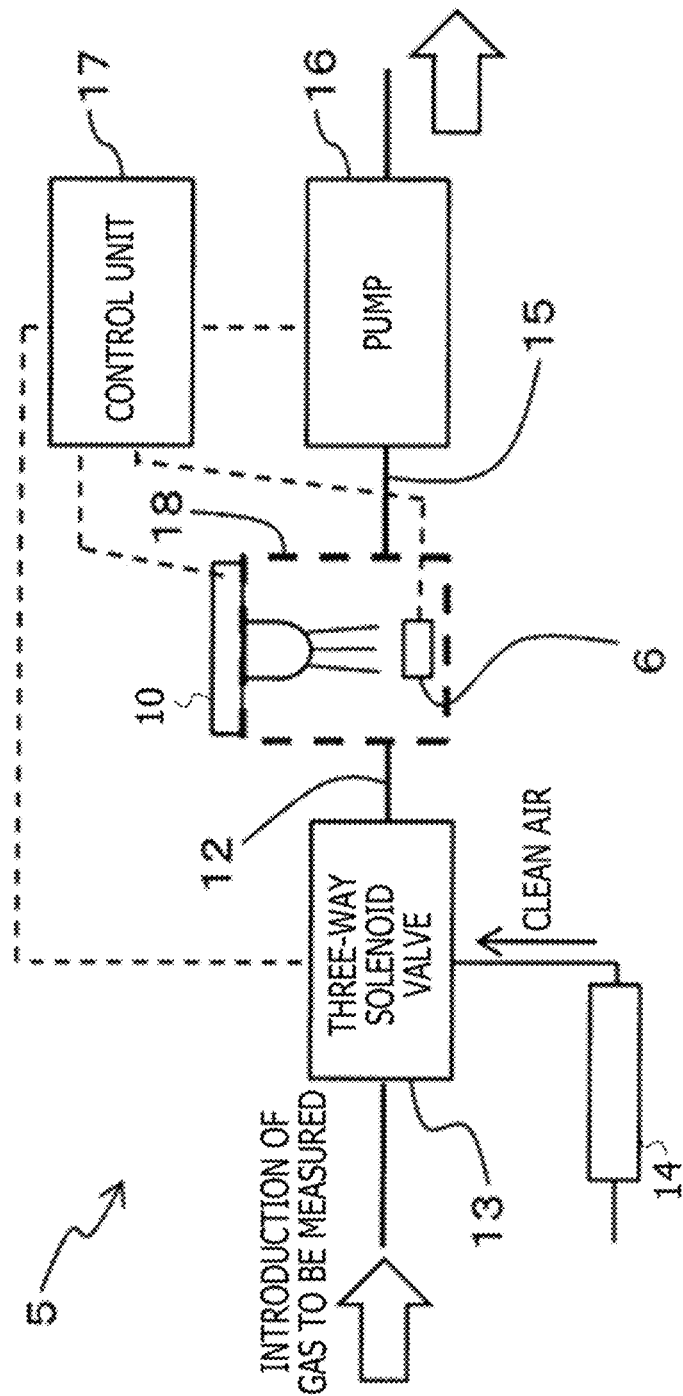
FIG. 33 is a diagram illustrating a configuration of the gas sensor according to the present embodiment.

Then, as illustrated in FIG. 2, when the gas sensor cartridge 1 is attached to the gas sensor body 20, the gas sensor cartridge 1 is provided between the inlet 21 and the outlet 22 of the gas sensor body 20, and the case 26 of the gas sensor cartridge 1 functions as the gas sensor chamber 18 (see FIG. 33, for example).

Furthermore, the inlet 21 and the outlet 22 are each provided with a check valve (not illustrated).

Furthermore, a gas to be measured is introduced from the inlet 21 into the case 26 (gas sensor chamber 18) of the gas sensor cartridge 1.

Furthermore, in a case of introducing dean air, the dean air is introduced into the case 26 (gas sensor chamber 18) of the gas sensor cartridge 1 from the inlet 21 through the filter 14.

Note that, here, a solenoid valve 13 is provided in the gas supply-side pipe 12 (see FIG. 33, for example) so as to be able to switch a path between a path passing through the filter 14 and a path not passing through the filter 14.

Furthermore, when the pump (blower pump) 16 is activated, an internal pressure inside the case 26 (inside the gas sensor chamber 18) of the gas sensor cartridge 1 rises, and the gas inside the case 26 (inside the gas sensor chamber 18) of the gas sensor cartridge 1 can be discharged while blocking gas inflow from the inlet 21.

Furthermore, the external connection terminal 27 provided in the gas sensor cartridge 1 is electrically connected to the control unit 17 (for example, an electric circuit) provided in the gas sensor body 20.

For example, the control unit 17 may include: an impedance measurement circuit including, for example, an AD converter and the like; and a microcomputer inducing a microprocessor unit (MPU) as an arithmetic circuit, and a memory. Note that the impedance measurement circuit is also referred to as a resistance measurement unit or a measurement unit.

Additionally, the external connection terminal 27 of the gas sensor cartridge 1 may be connected to the impedance measurement circuit constituting the control unit 17; the impedance measurement circuit may be connected to the MPU; various calculations such as calculation of a gas concentration and the like are performed by the MPU; data may be stored in the memory; and the data may be exchanged by a transceiver provided as the wireless unit 19.

By the way, in the present embodiment, when the gas sensor cartridge 1 is attached to the gas sensor body 20, the gas supply-side pipe 12 provided in the gas sensor body 20 is connected to the intake port 24 of the case 26 and the exhaust-side pipe 15 provided in the gas sensor body 20 is connected to the exhaust port 25 of the case 26.

Figure 3A:
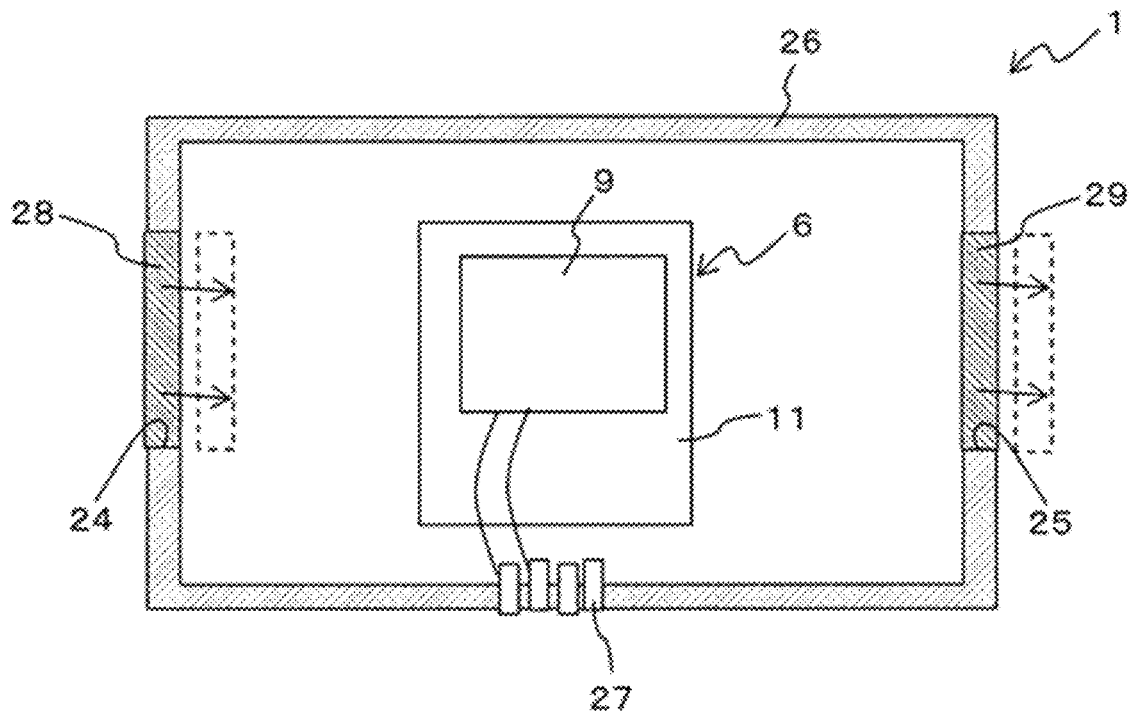
FIGS. 3A and 3B are schematic cross-sectional views illustrating the configuration of the gas sensor cartridge according to the present embodiment.
Figure 3B:
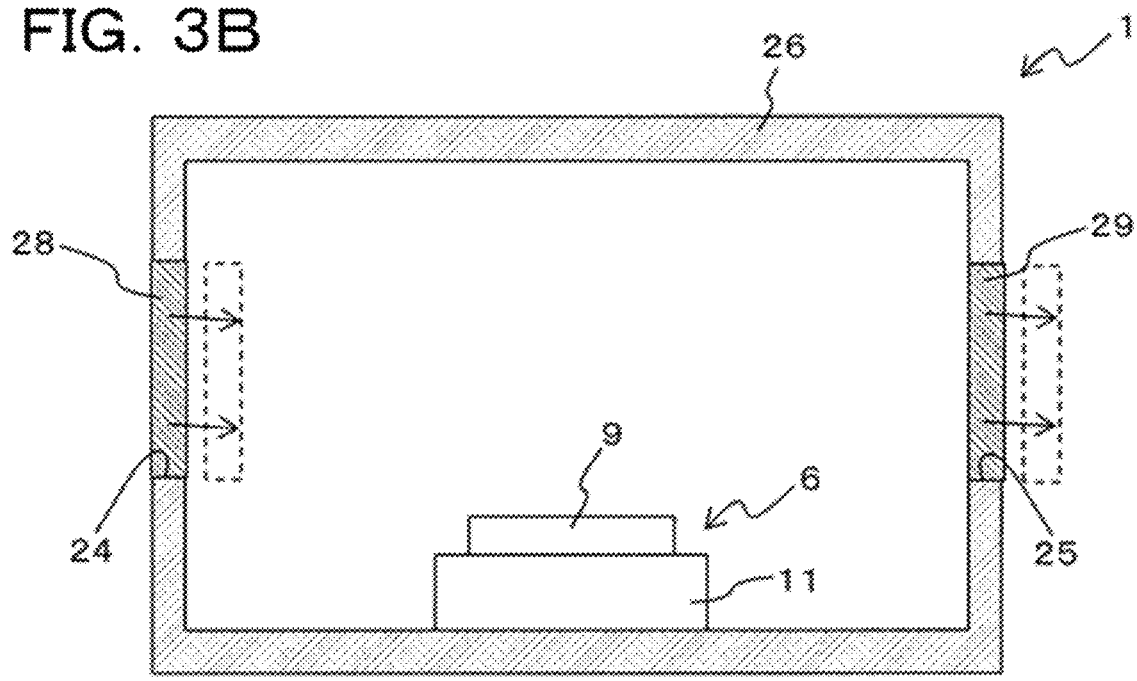

Furthermore, as illustrated in FIGS. 3A and 3B, the gas sensor cartridge 1 also includes: a first sealing member 28 that seals the intake port 24; and a second sealing member 29 that seals the exhaust port 25.

Here, the first sealing member 28 seals the intake port 24 in a manner such that the intake port 24 is opened when the gas sensor cartridge 1 is attached to the gas sensor body 20. Furthermore, the second sealing member 29 seals the exhaust port 25 in a manner such that the exhaust port 25 is opened when the gas sensor cartridge 1 is attached to the gas sensor body 20. Consequently, a periphery of the gas sensor device 6 is airtightly closed.

Figure 29:
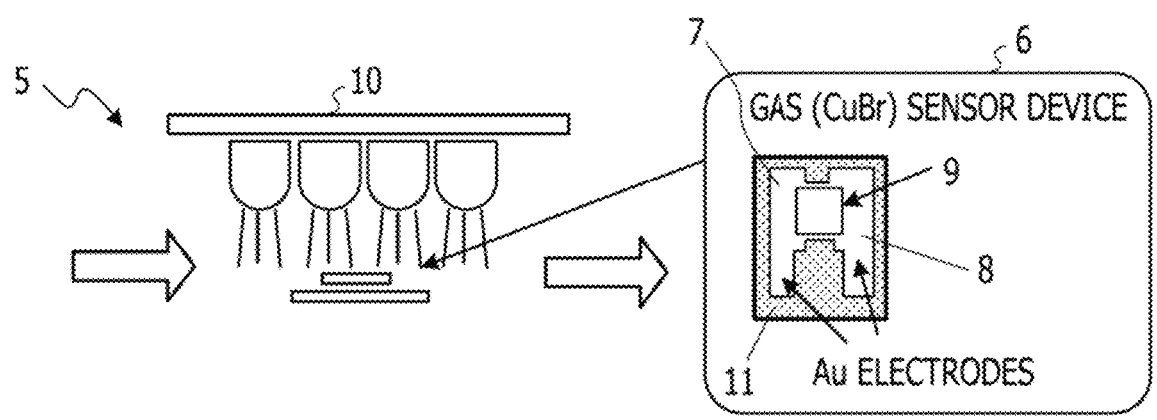
FIG. 29 is a schematic diagram illustrating the configuration of the gas sensor according to the present embodiment.

Note that the gas sensor device (CuBr sensor device) 6 is provided on a substrate 11 and includes: a first electrode 7; a second electrode 8; and a sensitive film (a film including a gas sensitive material) 9 that connects the first electrode 7 and the second electrode 8 (see FIG. 29, for example). Note that the first electrode 7 and the second electrode 8 are not illustrated in FIGS. 3A and 3B.

By the way, a light source is provided in the gas sensor body 20 or the gas sensor cartridge 1 in a case where the gas sensor 5 includes a light irradiation mechanism constituting a purifying mechanism or the like that performs purification by, for example, light irradiation. Note that the light source is also referred to as a light source element.

Figure 4:
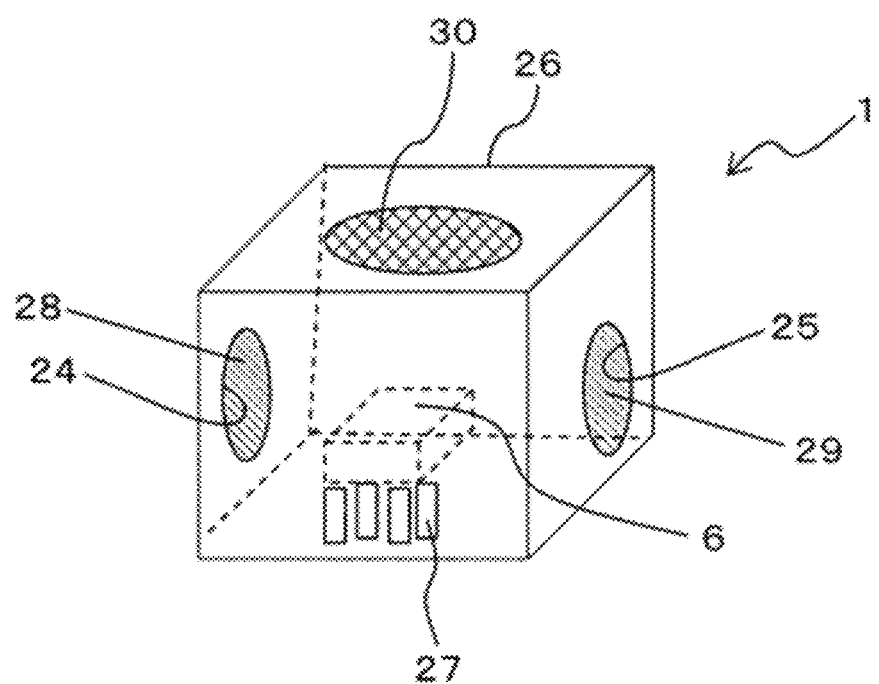
FIG. 4 is a schematic perspective view illustrating the configuration of the gas sensor cartridge according to the present embodiment.
Figure 5:
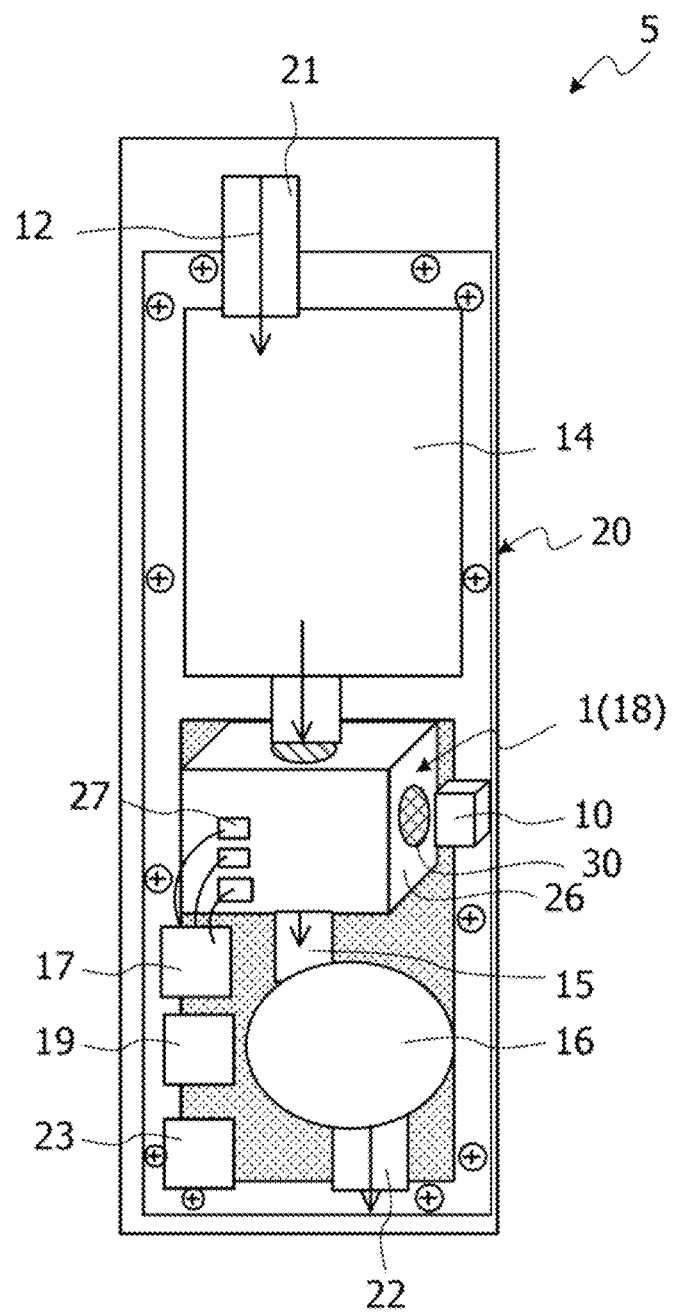
FIG. 5 is a schematic diagram illustrating the configuration of the gas sensor according to the present embodiment.

In this case, for example, the light source 10 may be provided in the gas sensor body 20; and the gas sensor cartridge 1 (here, the case 26) may include an optical window 30 as illustrated in FIGS. 4 to 6.

Then, when the gas sensor cartridge 1 is attached to the gas sensor body 20, a position of the light source 10 provided in the gas sensor body 20 and a position of the optical window 30 provided in the gas sensor cartridge 1 may be aligned with each other such that the gas sensor device 6 is irradiated with the light from the light source 10 through the optical window 30.

Furthermore, in a case of irradiating the gas sensor device 6 with light including ultraviolet (UV), the optical window 30 is to have a property to transmit the light including the UV.

In this case, a UV-LED (ultraviolet light-emitting diode) may be used as the light source 10, for example. Furthermore, for the optical window 30, for example, a glass member such as quartz glass, BK9, Pyrex (registered trademark) glass, and the like, or transparent acryl, polycarbonate, or the like may also be used.

Figure 6A:
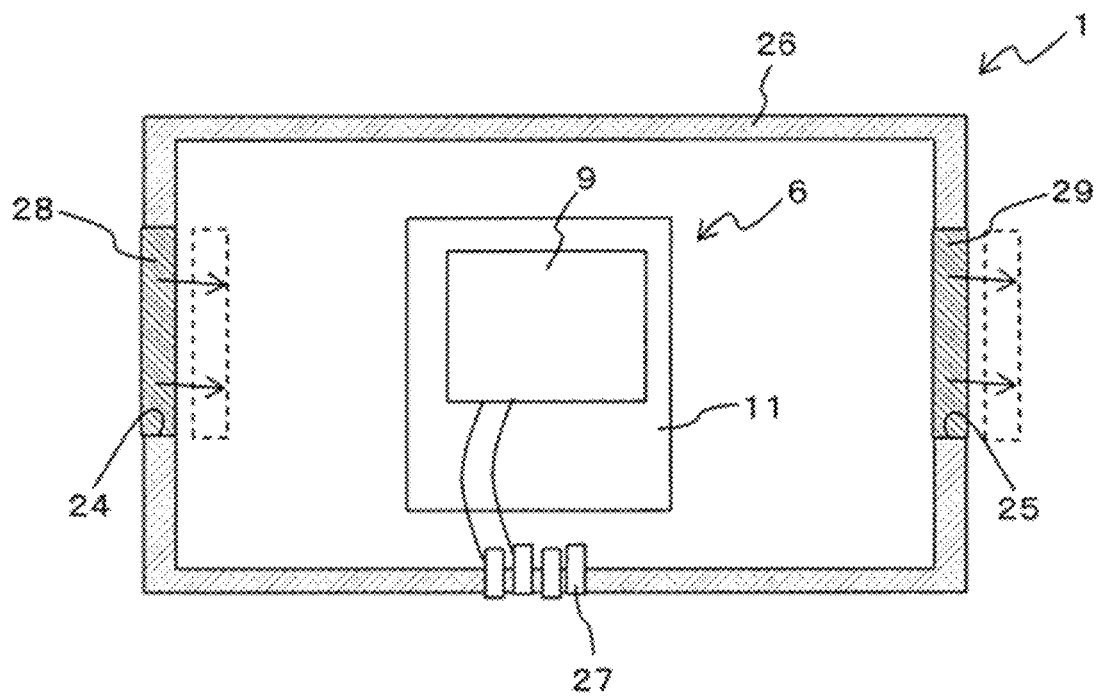
FIGS. 6A and 6B are schematic cross-sectional views illustrating the configuration of the gas sensor cartridge according to the present embodiment.
Figure 6B:
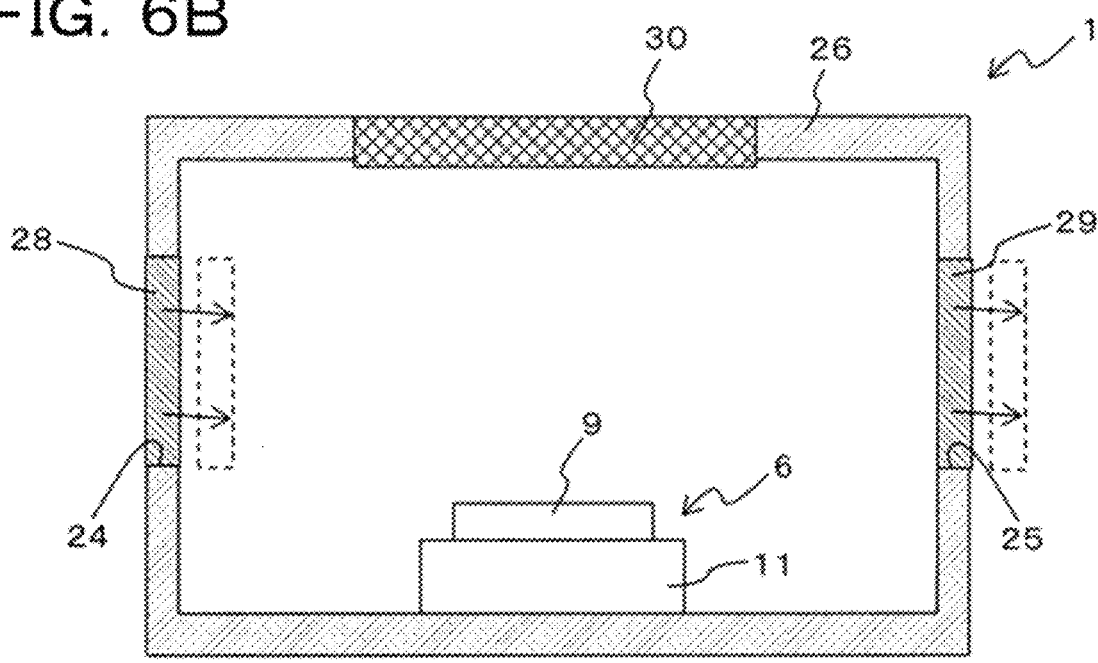

In this case, the optical window 30 may be provided on a side opposite to a side of the case 26 provided with the gas sensor device 6, for example, as illustrated in FIGS. 6A and 6B.

By the way, the first sealing member 28 is a first movable valve 31 capable of opening and closing the intake port 24 (see FIGS. 7A and 7B, for example) or a first protective film that is broken when the gas sensor cartridge 1 is attached to the gas sensor body 20. Furthermore, the second sealing member 29 is a second movable valve 32 capable of opening and closing the exhaust port 25 (see FIGS. 7A and 7B, for example) or a second protective film that is broken when the gas sensor cartridge 1 is attached to the gas sensor body 20.

Here, in a case where the first sealing member 28 and the second sealing member 29 are the first movable valve 31 and the second movable valve 32, respectively (see FIGS. 7A and 7B, for example), the first movable valve 31 and the second movable valve 32 may be, for example, mechanically movable valves.

Figure 7A:
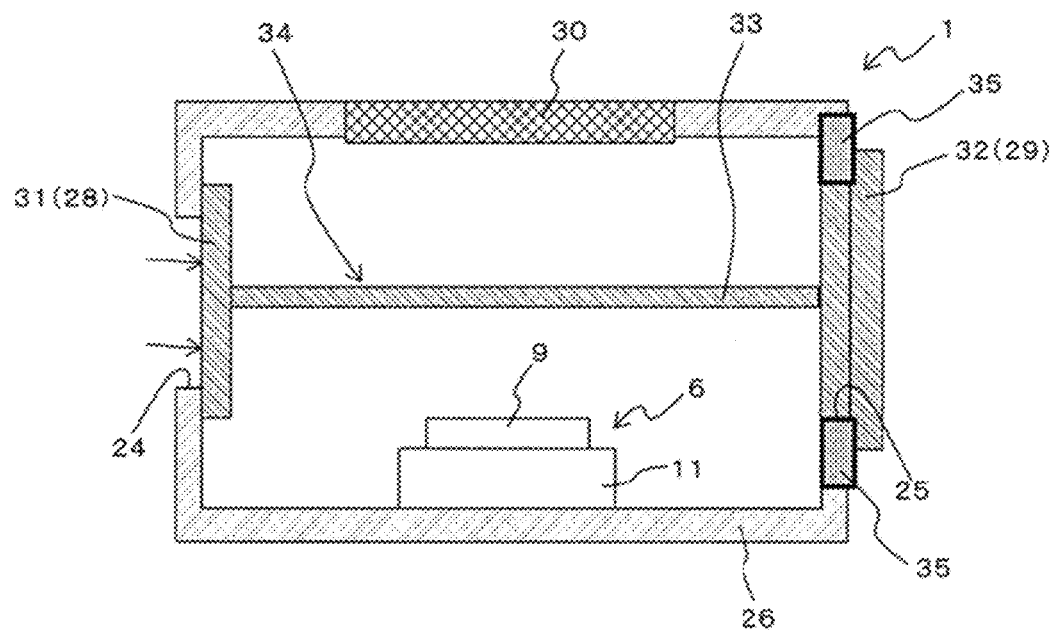
FIGS. 7A and 7B are schematic cross-sectional views illustrating the configuration of the gas sensor cartridge according to the present embodiment.
Figure 7B:
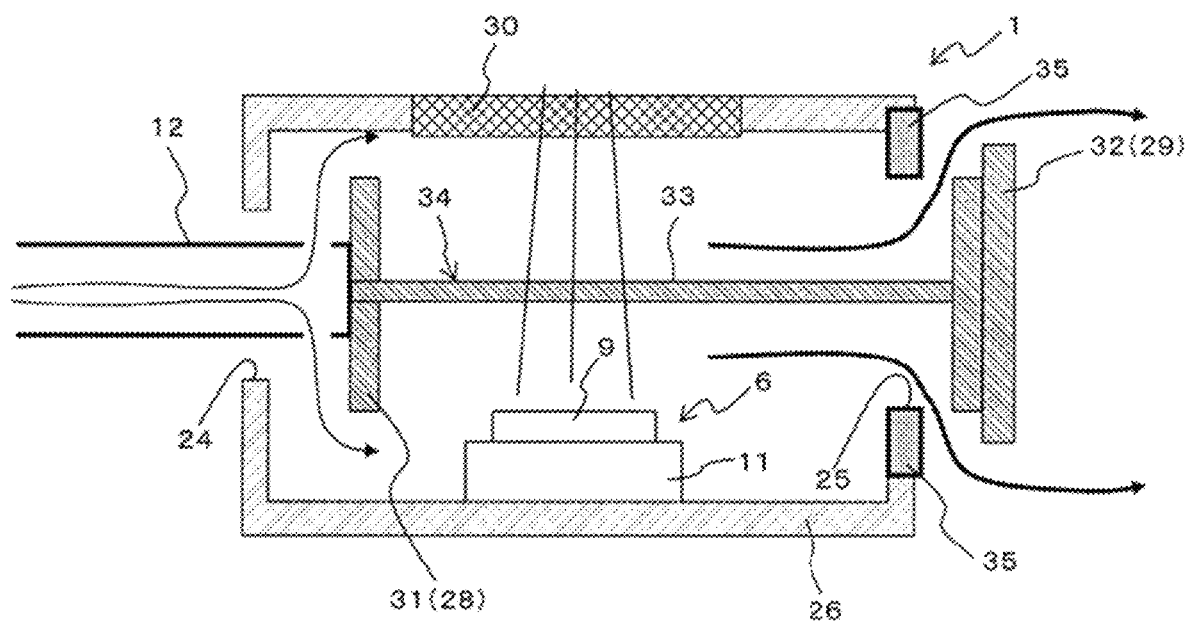

Note that the description is provided for FIGS. 7A and 7B by exemplifying the case where the gas sensor cartridge 1 includes the optical window 30, but a similar configuration may also be employed even in a case of not including the optical window.

For example, as illustrated in FIG. 7A, a valve member 34 that connects and incorporates the first movable valve 31 and the second movable valve 32 with a shaft 33 may be prepared; and the valve member 34 may be provided inside the case 26 such that an outer peripheral portion of the first movable valve 31 abuts on a periphery of the intake port 24 of the case 26 to seal the intake port 24 with the first movable valve 31 and such that an outer peripheral portion of the second movable valve 32 abuts on a periphery of the exhaust port 25 of the case 26 to seal the exhaust port 25 with the second movable valve 32.

Furthermore, for example, at least the second movable valve 32 may be made from metal; and a magnet 35 may be provided, for example, in a periphery of the exhaust port 25 of the case 26 so as to keep a state in which the intake port 24 is sealed with the first movable valve 31 and the exhaust port 25 is sealed with the second movable valve 32 by the second movable valve 32 sticking to the magnet 35.

Then, when the gas sensor cartridge 1 is attached to the gas sensor body 20, the valve member 34 may be moved by the first movable valve 31 being pushed by the gas supply-side pipe 12 (for example, a tube) provided on the gas sensor body 20 side as illustrated in FIG. 7B such that: the outer peripheral portion of the first movable valve 31 is separated from the periphery of the intake port 24 of the case 26 so as to open the intake port 24; and the outer peripheral portion of the second movable valve 32 is separated from the magnet 35 provided in the periphery of the exhaust port 25 of the case 26 so as to open the exhaust port 25.

On the other hand, when the gas sensor cartridge 1 is detached from the gas sensor body 20, the intake port 24 may be returned to the state sealed with the first movable valve 31 and the exhaust port 25 may be returned to the state sealed with the second movable valve 32 by the second movable valve 32 sticking to the magnet 35 provided in the periphery of the exhaust port 25 of the case 26 when the gas supply-side pipe 12 (for example, the tube) provided on the gas sensor body 20 side is separated from the first movable valve 31.

With such a configuration, the gas sensor cartridge 1 may be used repeatedly by attaching/detaching the gas sensor cartridge 1 to/from the gas sensor body 20.

Note that, not limited to such a configuration, for example, at least the first movable valve 31 may be made from metal, and a magnet may be provided in the periphery of the intake port 24 of the case 26. Furthermore, for example, the entire valve member 34 may be made from metal, or may be partly made from metal. Furthermore, when the gas sensor cartridge 1 is attached to the gas sensor body 20, the second movable valve 32 may also be pushed by the exhaust-side pipe 15 (for example, a tube) provided on the gas sensor body 20 side. Furthermore, for example, a spring or the like may be used instead of the magnet 35. In this case, the material of the valve member 34 may not be made from metal, and for example, a resin or the like inert to the gas to be measured may also be sued.

Furthermore, to accurately perform position alignment between the light source 10 and the optical window 30, for example, it is preferable to: provide the gas sensor body 20 with the gas sensor socket 36 to which the gas sensor cartridge 1 can be inserted; and provide this gas sensor socket 36 with the light source 10 as illustrated in FIGS. 8A and 80.

In this case, it becomes easy to detach/attach the gas sensor cartridge 1 because the position alignment between the light source 10 and the optical window 30 can be accurately performed and the intake port 24 and the exhaust port 25 can be also opened by simply inserting the gas sensor cartridge 1 into the gas sensor socket 36.

Note that the gas sensor cartridge 1 may include the light source 10 installed at outside of the optical window 30 instead of providing the light source 10 in the gas sensor body 20. For example, the gas sensor cartridge 1 may have the light source 10 installed at the outside thereof.

Furthermore, in a case where the first sealing member 28 and the second sealing member 29 are the first protective film and the second protective film, respectively, each of the first protective film and the second protective film may be a film such as an aluminum film or the like.

For example, the intake port 24 may be sealed with a first film as the first protective film by pasting the first film to the periphery of the intake port 24 of the case 26; and the exhaust port 25 may be sealed with a second film as the second protective film by pasting the second film to the periphery of the exhaust port 25 of the case 26.

Then, when the gas sensor cartridge 1 is attached to the gas sensor body 20, the intake port 24 may be opened by the first film being broken by the gas supply-side pipe 12 (for example, the tube) provided on the gas sensor body 20 side; and the exhaust port 25 may be also opened by the second film being broken by the exhaust-side pipe 15 (for example, the tube) provided on the gas sensor body 20 side.

Thus, the inside of the case 26 including the gas sensor device 6 is in the state sealed with the first sealing member 28 and the second sealing member 29 until the gas sensor cartridge 1 is attached to the gas sensor body 20.

Then, when the gas sensor cartridge 1 is attached to the gas sensor body 20, the gas supply-side pipe 12 provided in the gas sensor body 20 is connected to the intake port 24 of the case 26, the exhaust-side pipe 15 provided in the gas sensor body 20 is connected to the exhaust port 25 of the case 26, and the case 26 directly functions as the gas sensor chamber 18 (see FIG. 33, for example).

For example, here, the gas sensor chamber 18 provided in the gas sensor 5 is made to serve as the gas sensor cartridge 1.

In this case, the inside of the case 26 serves as a measurement chamber, the measurement chamber is connected between the intake port 24 and the exhaust port 25, and the gas sensor device 6 is arranged in the measurement chamber.

Thus, since the gas sensor device 6 has a structure that can be replaced without contacting the outside air, fluctuations in the characteristics of the gas sensor device 6 may be reduced.

Figure 9:
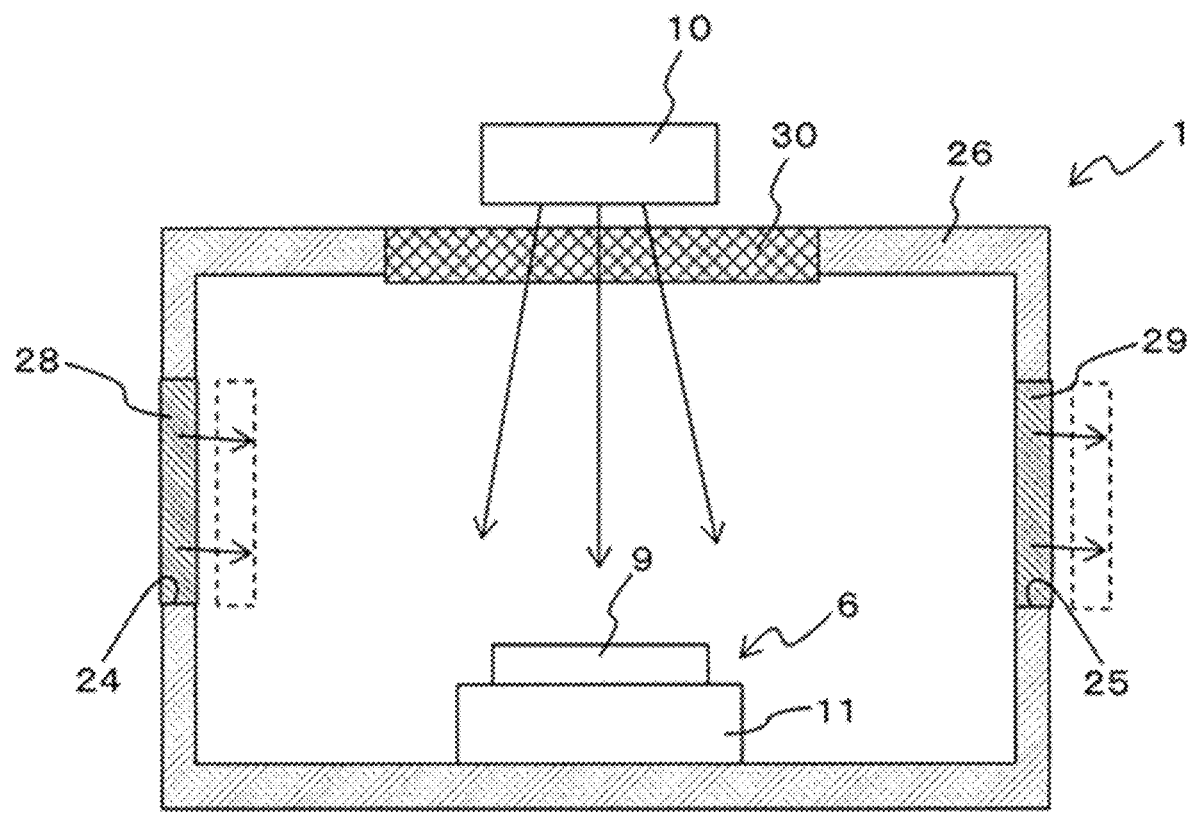
FIG. 9 is a schematic cross-sectional view illustrating the configuration of the gas sensor cartridge, and a light source provided in the gas sensor body according to the present embodiment.

By the way, in a case where the position of the light source 10 provided in the gas sensor body 20 and the position of the optical window 30 provided in the gas sensor cartridge 1 are aligned with each other when the gas sensor cartridge 1 is attached to the gas sensor body 20, the gas sensor device 6 is irradiated with the light from the light source 10 through the optical window 30 as illustrated in FIG. 9, for example.

Figure 10:
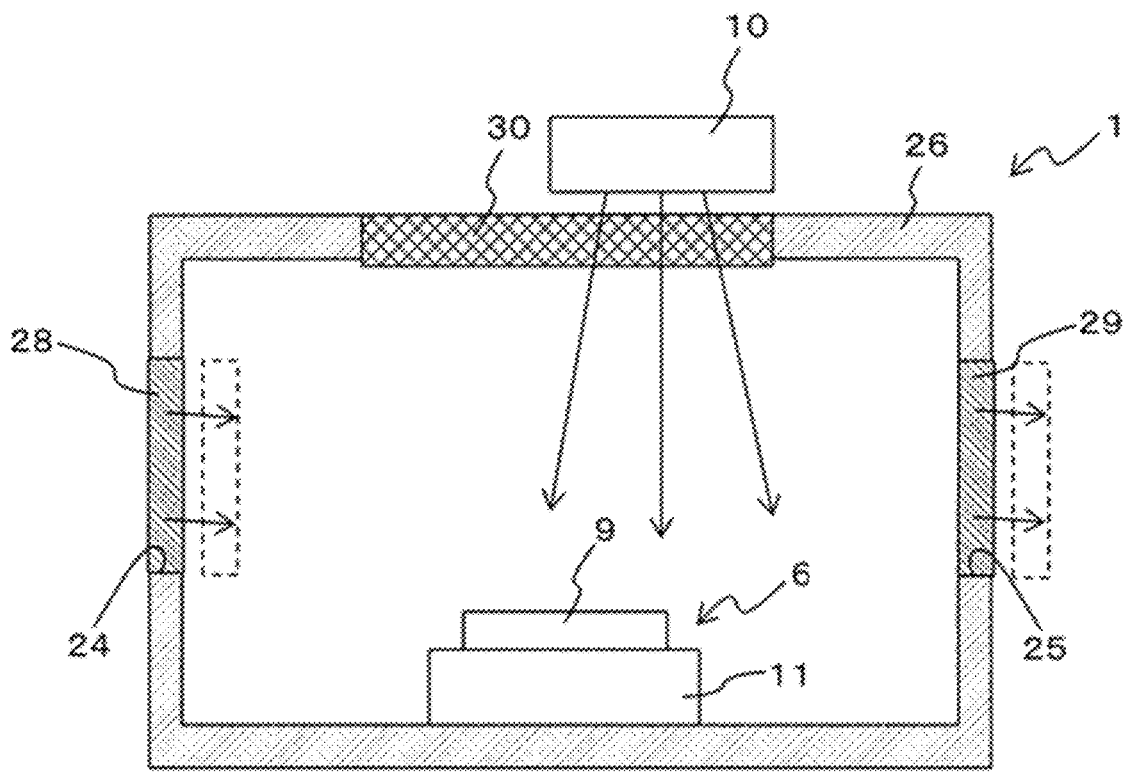
FIG. 10 is a schematic cross-sectional view illustrating a state in which a position of the gas sensor cartridge and a position of the light source provided in the gas sensor body are misaligned according to the present embodiment.

However, in a case where the position of the light source 10 provided in the gas sensor body 20 and the position of the optical window 30 provided in the gas sensor cartridge 1 are misaligned from each other when the gas sensor cartridge 1 is attached to the gas sensor body 20, it may be considered that the gas sensor device 6 is hardly irradiated with the light from the light source 10 through the optical window 30 as illustrated in FIG. 10, for example.

Figure 11:
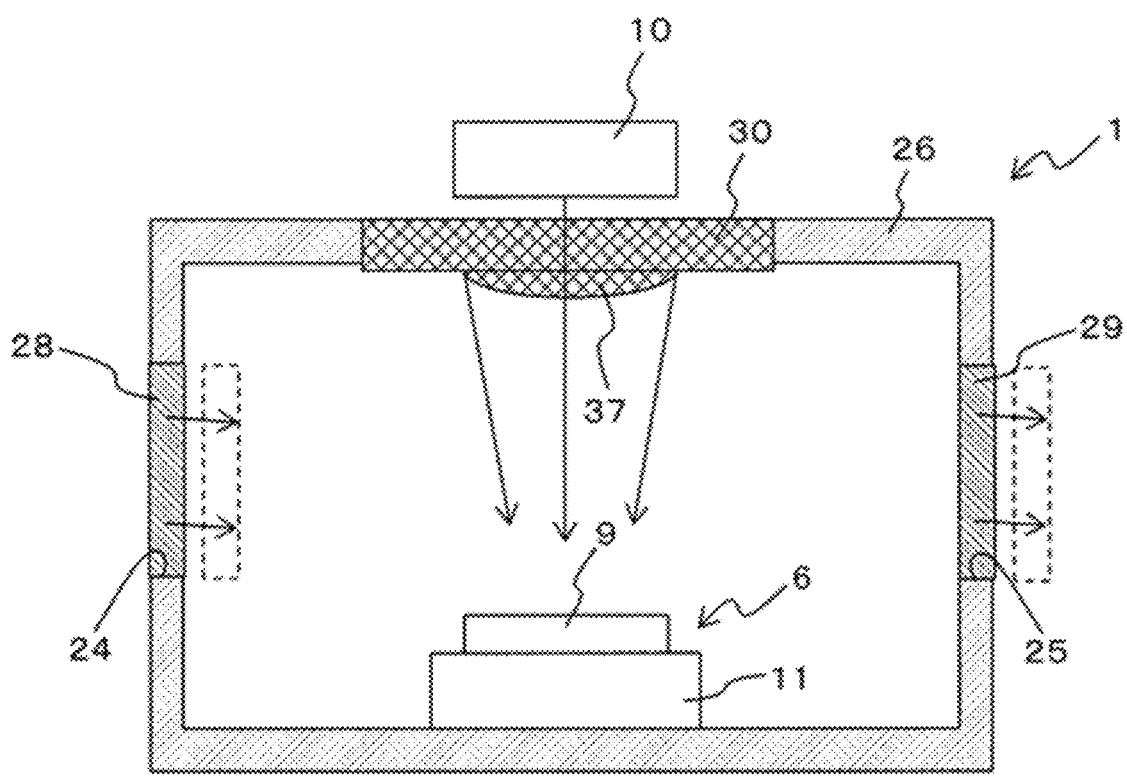
FIG. 11 is a schematic cross-sectional view illustrating a configuration of the gas sensor cartridge, and the light source provided in the gas sensor body according to the present embodiment.
Figure 12:
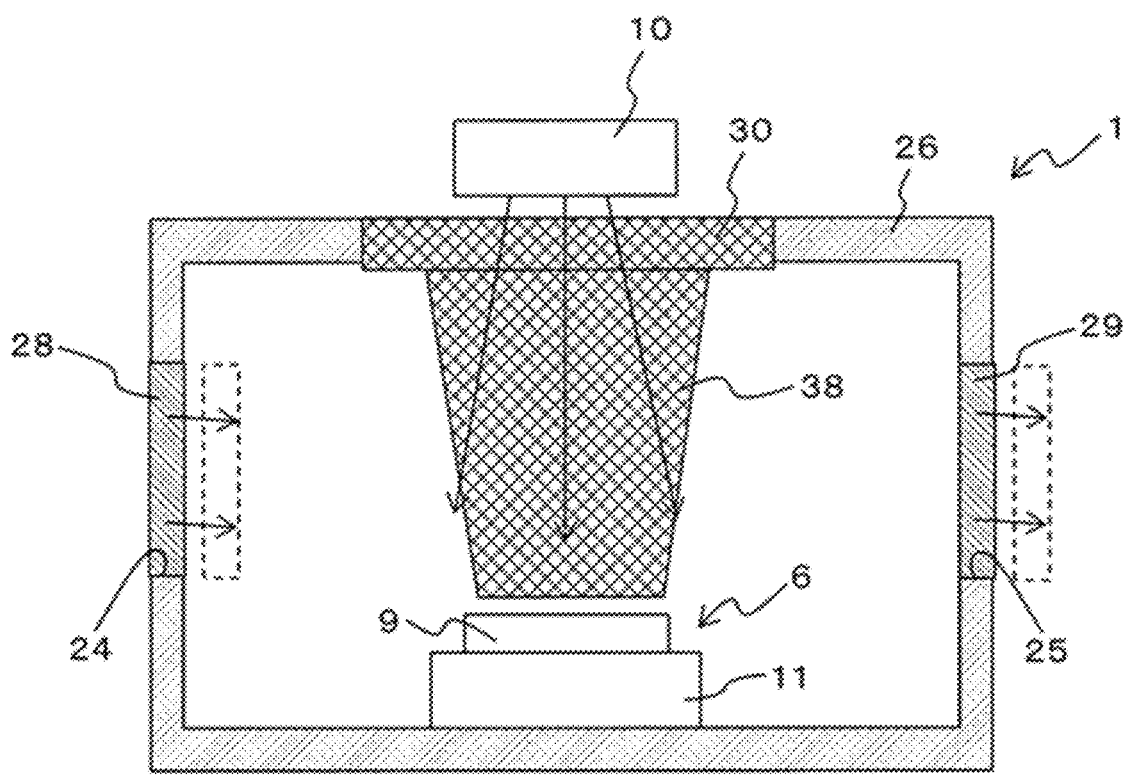
FIG. 12 is a schematic cross-sectional view illustrating a configuration of the gas sensor cartridge and the light source provided in the gas sensor body according to the present embodiment.

In this case, for example, a condenser lens 37 (for example, a lens such as a convex lens, a Fresnel lens, or the like) or an optical waveguide member 38 may be provided on an inner surface of the optical window 30 or between the optical window 30 and the gas sensor device 6 as illustrated in FIGS. 11 and 12.

Note that, as materials for these, for example, not only glass members such as quartz glass, BK9, Pyrex (registered trademark) glass, and the like, but also transparent acryl, polycarbonate, and the like may also be used.

Consequently, even in a case where the position of the gas sensor cartridge 1 is misaligned when the gas sensor cartridge 1 is attached to the gas sensor body 20, the gas sensor device 6 may be able to be reliably irradiated with the light from the light source 10.

Furthermore, since the condenser lens (lens) 37 or the optical waveguide member 38 is provided in a space between the optical window 30 and the gas sensor device 6, the gas to be measured may be more exposed to the gas sensor device 6 or a flow rate of the gas to be measured may be increased. Consequently, effective measurement may be performed.

For example, as illustrated in FIG. 11, the condenser lens (lens) 37 may be provided on the inner surface of the optical window 30. For example, the condenser lens 37 integrally formed on the inner surface of the optical window 30 may be used. In this case, a portion of the condenser lens 37 is also referred to as a condenser lens region.

Furthermore, the condenser lens (lens) 37 may be provided between the optical window 30 and the gas sensor device 6, for example, in a space between the surface of the optical window 30 and the surface of the gas sensor device 6 in a manner separated from the optical window 30.

Furthermore, for example, the optical waveguide member 38 may be provided on the inner surface of the optical window 30 as illustrated in FIG. 12. For example, it is also possible to use the optical waveguide member 38 integrally formed on the inner surface of the optical window 30. In this case, a portion of the optical waveguide member 38 is also referred to as an optical waveguide region.

Furthermore, the optical waveguide member 38 may be provided between the optical window 30 and the gas sensor device 6, for example, in the space between the surface of the optical window 30 and the surface of the gas sensor device 6 separately from the optical window 30.

Note that the gas sensor cartridge 1 may include the light source 10 installed at the outside of the optical window 30 instead of providing the light source 10 in the gas sensor body 20 in the configuration as illustrated in FIG. 11 or FIG. 12. For example, the gas sensor cartridge 1 may have the light source 10 installed at the outside thereof.

Furthermore, for example, the gas sensor device 6 may be irradiated only with light having a wavelength necessary for the gas sensor device 6 by providing a bandpass filter (BPF) between the optical window 30 and the gas sensor device 6 so as to irradiate the gas sensor device 6 with the light from the light source 10 through the bandpass filter.

Figure 13:
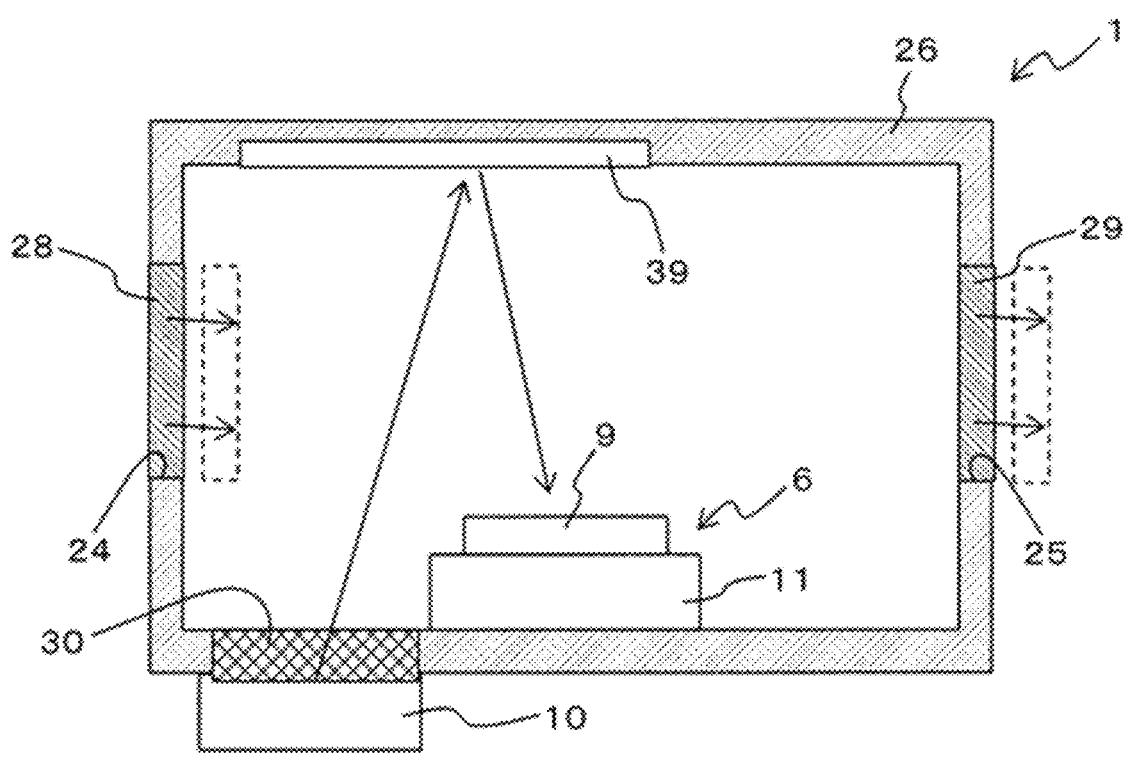
FIG. 13 is a schematic cross-sectional view illustrating configurations of the gas sensor cartridge and the light source installed therein according to the present embodiment.

Note that, not limited thereto, the optical window 30 may be provided on the side of the case 26 provided with the gas sensor device 6 as illustrated, for example, in FIG. 13.

Additionally, a reflection mirror 39 that reflects light incident from the optical window 30 toward the gas sensor device 6 may be provided on the side opposite to the side of the case 26 provided with the gas sensor device 6.

Figure 14:
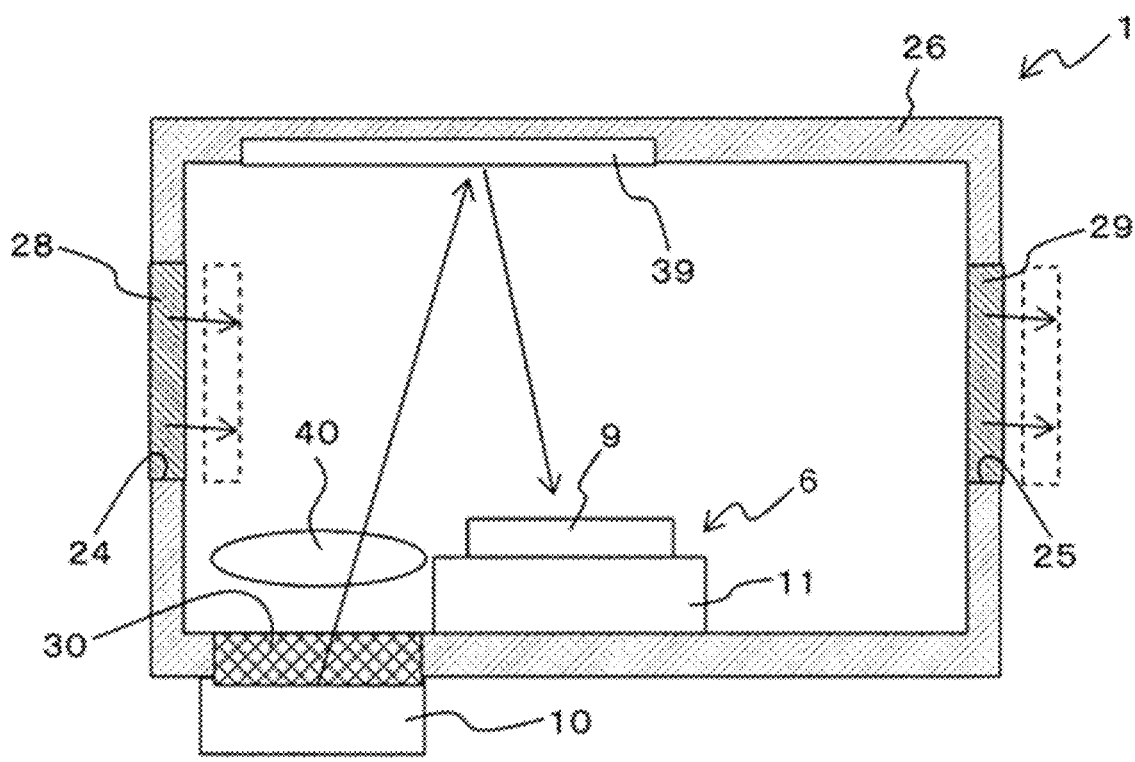
FIG. 14 is a schematic cross-sectional view illustrating configurations of the gas sensor cartridge and the light source installed therein according to the present embodiment.

In the case of having such a configuration also, a condenser lens (lens) 40 or an optical waveguide member provided on an optical path from the optical window 30 to the gas sensor device 6 may be provided as illustrated, for example, in FIG. 14.

Alternatively, the gas sensor cartridge 1 may include the light source 10 installed at the outside of the optical window 30 as illustrated in FIG. 13 or FIG. 14. Thus, the gas sensor cartridge 1 may have the light source 10 installed at the outside thereof. Note that, not limited thereto, the light source 10 may be provided in the gas sensor body 20.

Figure 15:
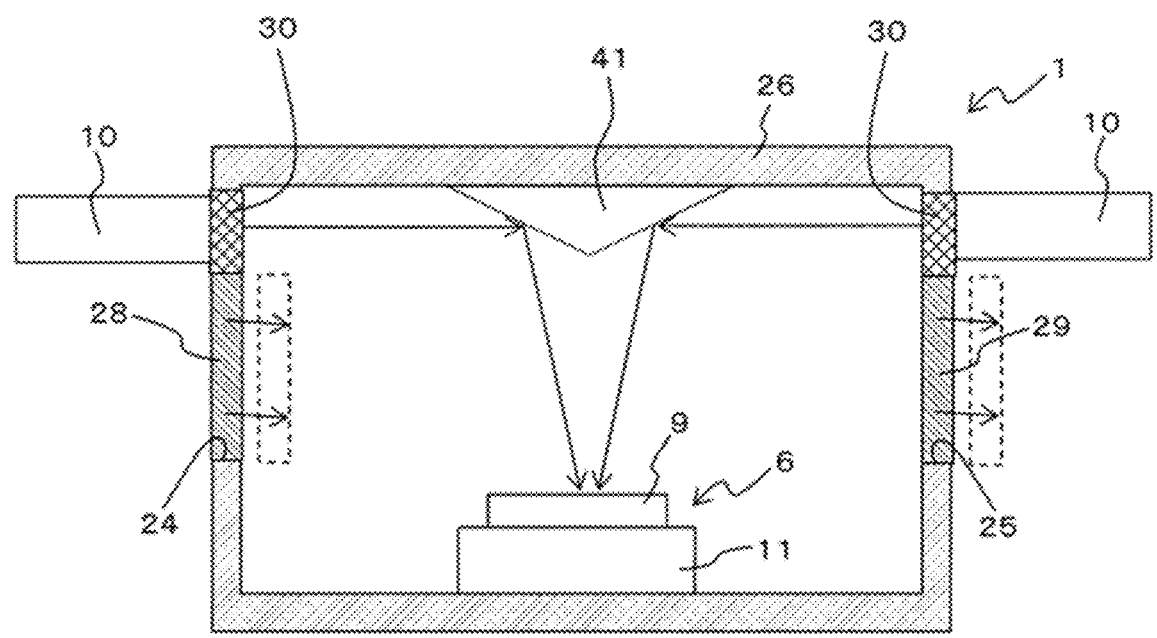
FIG. 15 is a schematic cross-sectional view illustrating configurations of the gas sensor cartridge and the light source installed therein according to the present embodiment.

Alternatively, as illustrated in FIG. 15, for example, the optical window 30 may be provided on a side portion orthogonal to a bottom portion of the case 26 provided with the gas sensor device 6. Additionally, a reflection mirror 41 that reflects the light incident from the optical window 30 toward the gas sensor device 6 may be provided on the side opposite to the side of the case 26 provided with the gas sensor device 6.

In the case of having such a configuration also, a condenser lens or an optical waveguide member provided on the optical path from the optical window 30 to the gas sensor device 6 may be provided.

Alternatively, the gas sensor cartridge 1 may include the light source 10 installed at the outside of the optical window 30. Thus, the gas sensor cartridge 1 may have the light source 10 installed at the outside thereof. Note that, not limited thereto, the light source 10 may be provided in the gas sensor body 20.

By the way, the light source 10 is provided in the gas sensor body 20, and the case 26 of the gas sensor cartridge 1 is provided with the optical window 30 in the above-described embodiment, but not limited thereto, and the gas sensor cartridge 1 may include the light source 10 provided inside the case 26 as illustrated in FIGS. 16 to 20, for example. Thus, the light source 10 may be provided inside the gas sensor cartridge 1.

In a case of having such a configuration, the gas sensor cartridge 1 (here, the case 26) may not include the optical window 30.

In short, the gas sensor cartridge 1 (here, the case 26) may include either the optical window 30 or the light source 10.

Figure 16:
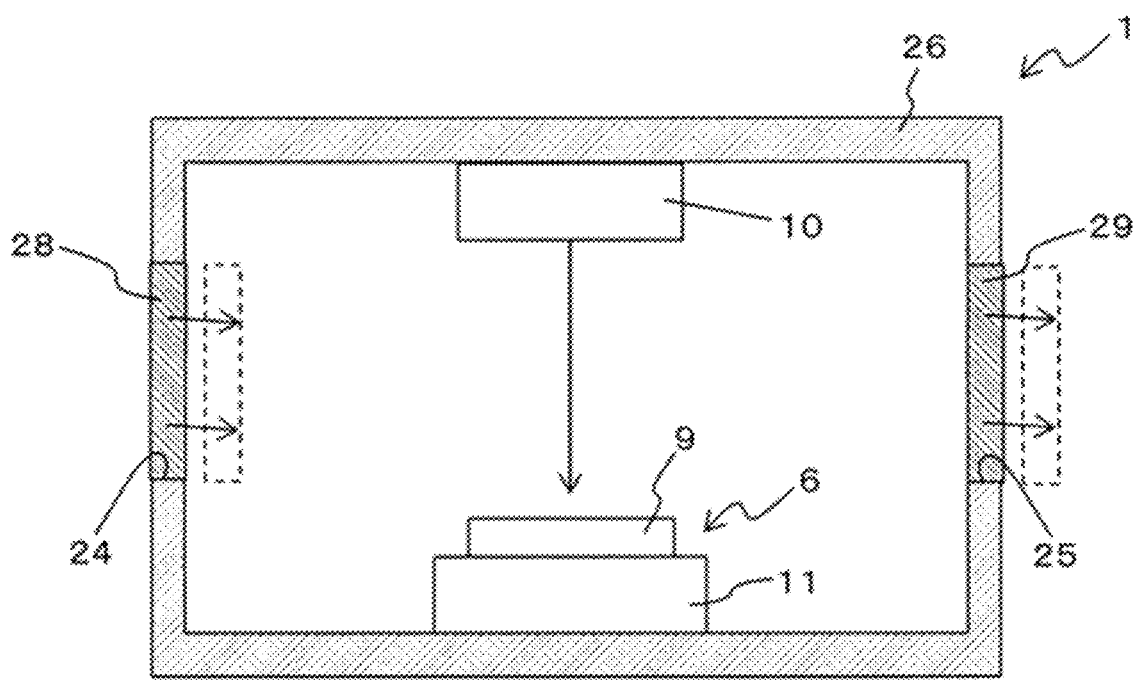
FIG. 16 is a schematic cross-sectional view illustrating configurations of the gas sensor cartridge and the light source provided inside thereof according to the present embodiment.

In this case, as illustrated in FIG. 16, for example, the light source 10 may be provided on the side opposite to the side of the case 26 provided with the gas sensor device 6.

Figure 17:
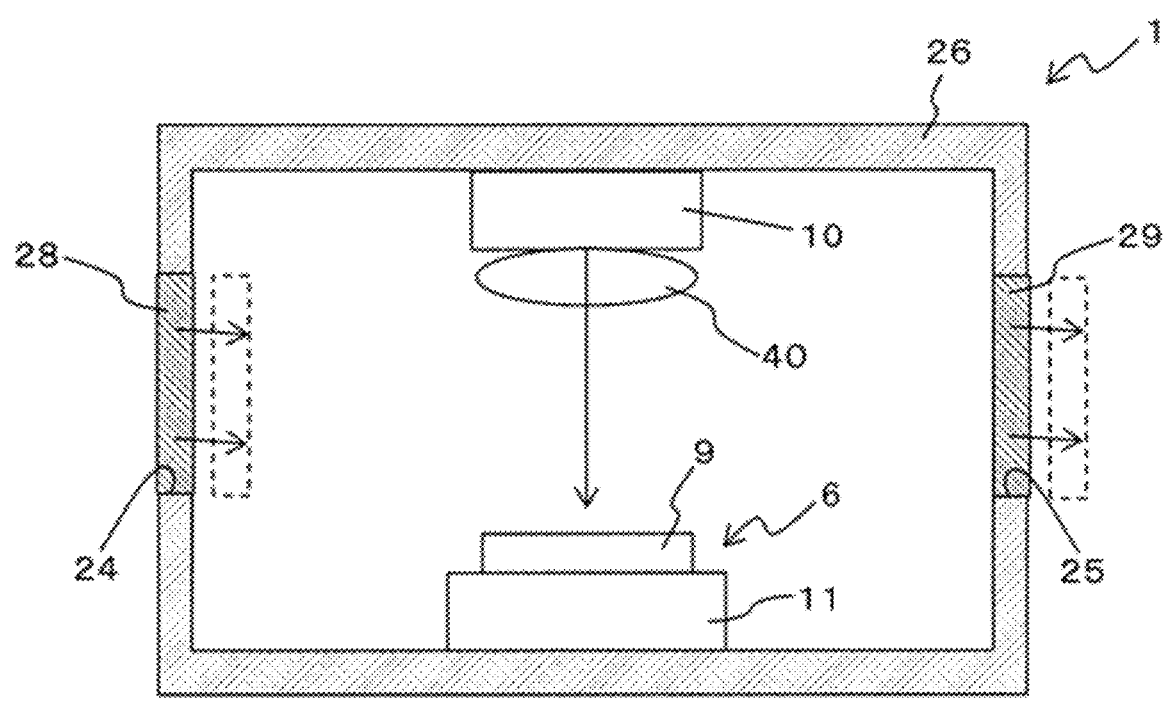
FIG. 17 is a schematic cross-sectional view illustrating configurations of the gas sensor cartridge and the light source provided inside thereof according to the present embodiment.

Alternatively, as illustrated in FIG. 17, for example, the condenser lens (lens) 40 or the optical waveguide member provided between the light source 10 and the gas sensor device 6 may be provided.

Figure 18:
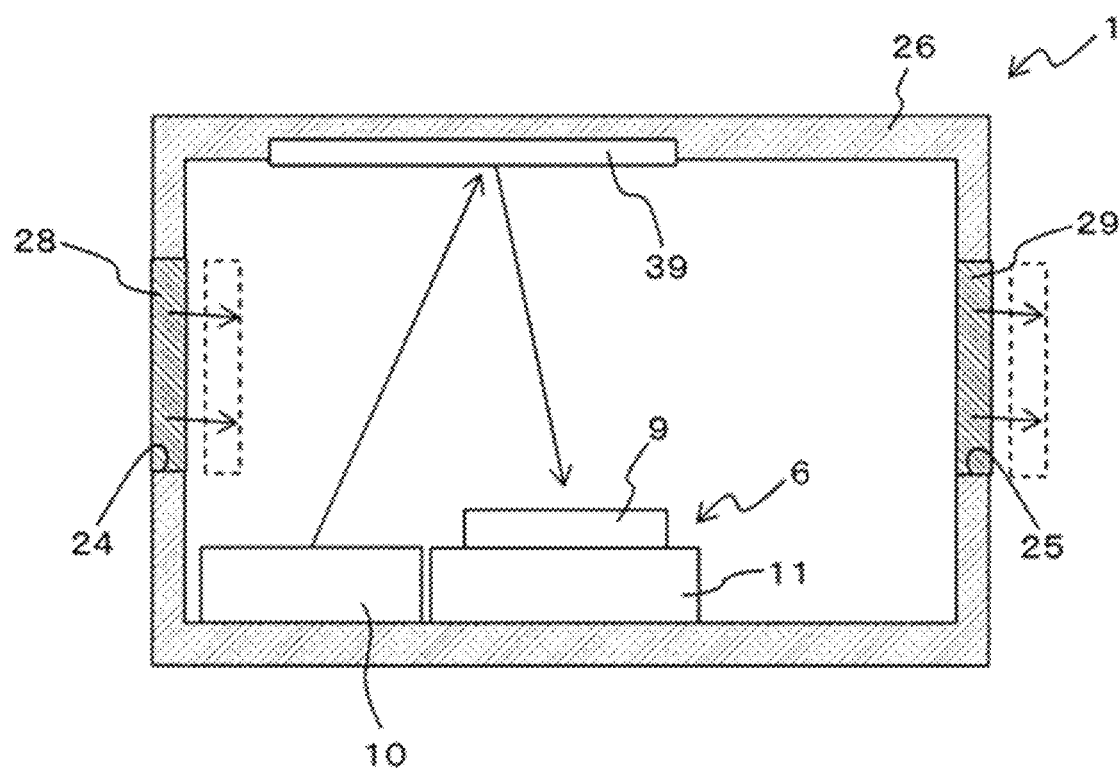
FIG. 18 is a schematic cross-sectional view illustrating configurations of the gas sensor cartridge and the light source provided inside thereof according to the present embodiment.

Alternatively, as illustrated in FIG. 18, for example, the light source 10 may be provided on the side of the case 26 provided with the gas sensor device 6.

Additionally, the reflection mirror 39 that reflects the light from the light source 10 toward the gas sensor device 6 may be provided on the side opposite to the side of the case 26 provided with the gas sensor device 6.

Figure 19:
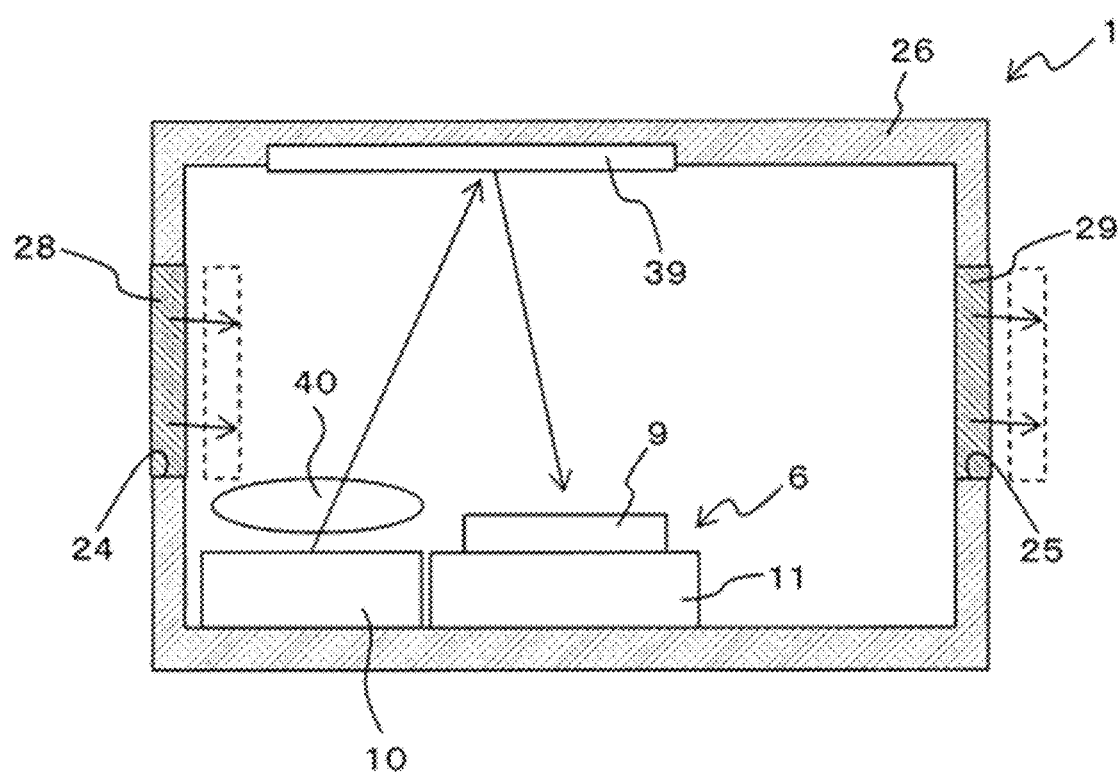
FIG. 19 is a schematic cross-sectional view illustrating configurations of the gas sensor cartridge and the light source provided inside thereof according to the present embodiment.

Alternatively, as illustrated in FIG. 19, for example, the condenser lens (lens) 40 or the optical waveguide member provided on the optical path from the light source 10 to the gas sensor device 6 may be provided.

Figure 20:
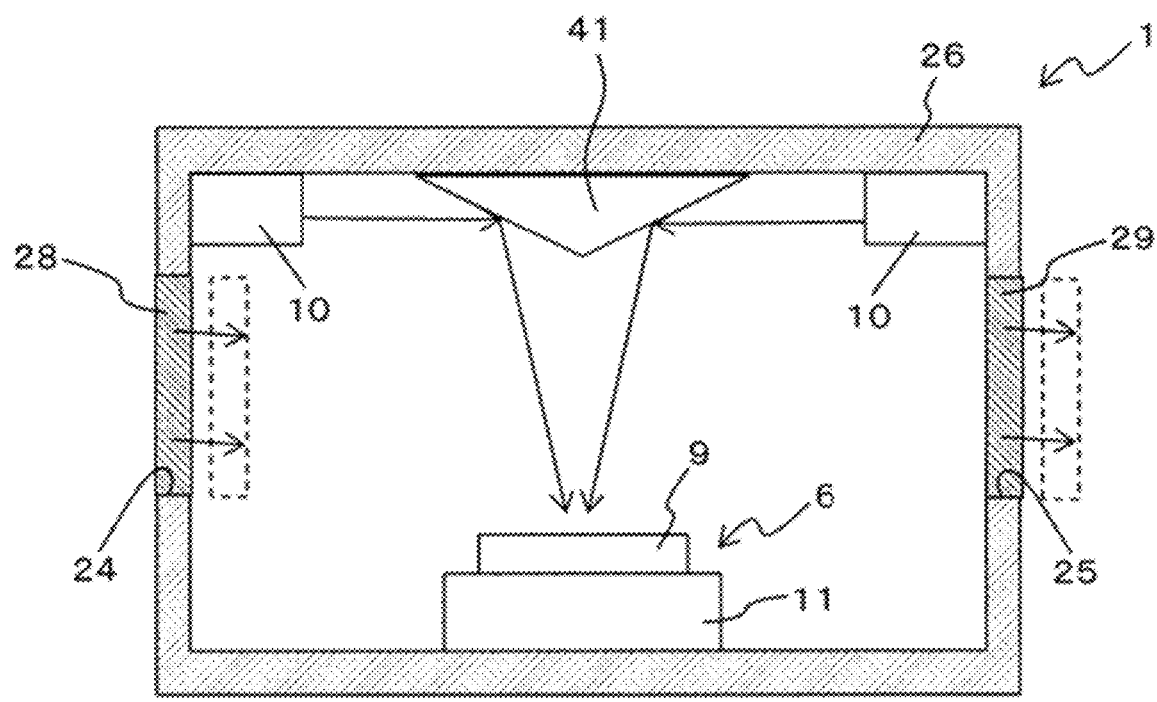
FIG. 20 is a schematic cross-sectional view illustrating configurations of the gas sensor cartridge and the light source provided inside thereof according to the present embodiment.

Alternatively, as illustrated in FIG. 20, for example, the light source 10 may be provided on the side portion orthogonal to the bottom portion of the case 26 provided with the gas sensor device 6.

Additionally, the reflection mirror 41 that reflects the light from the light source 10 toward the gas sensor device 6 may be provided on the side opposite to the side of the case 26 provided with the gas sensor device 6.

In a case of having such a configuration also, a condenser lens or an optical waveguide member provided on the optical path from the light source 10 to the gas sensor device 6 may be provided.

Figure 21:
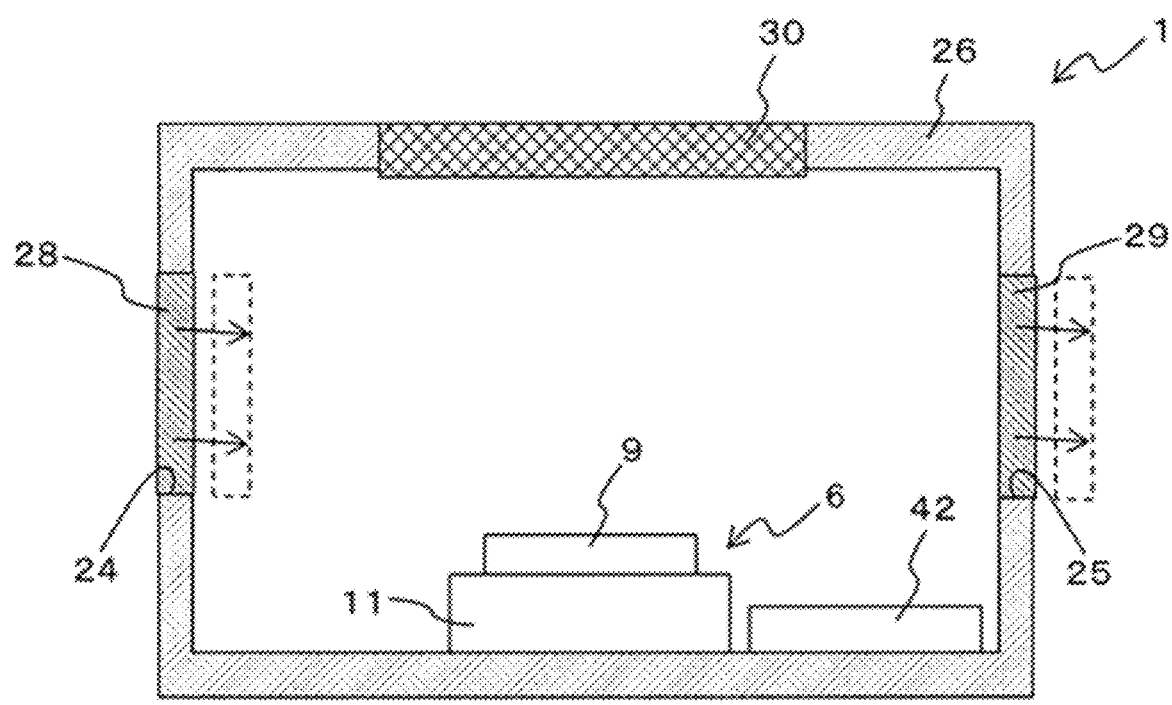
FIG. 21 is a schematic cross-sectional view illustrating configurations of the gas sensor cartridge and a gas adsorption member provided inside thereof according to the present embodiment.

By the way, as illustrated in FIG. 21, for example, it is preferable that the gas sensor cartridge 1 includes a gas adsorption member 42 provided inside the case 26.

Here, as the gas adsorption member 42, a hygroscopic agent such as zeolite, silica gel, or the like that may adsorb a gas may be provided.

Consequently, the gas inside the case 26 may be adsorbed, and deterioration of the gas sensor device 6 may be suppressed.

Note that FIG. 21 illustrates, as an example, a case where the gas adsorption member 42 is provided in the configuration illustrated in FIG. 6B, but not limited thereto, and it is preferable to provide the gas adsorption member 42 similarly in other configurations described above (see FIGS. 38, 7A, 8A, and 11 to 20, for example).

Figure 22:
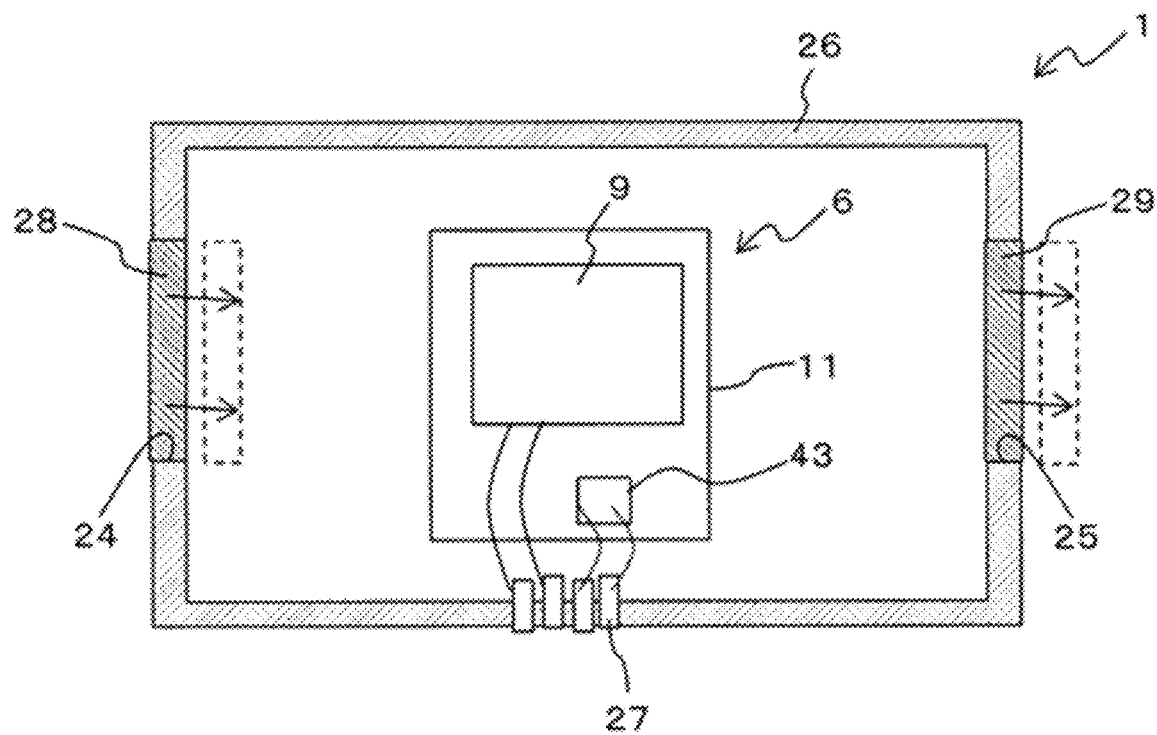
FIG. 22 is a schematic cross-sectional view illustrating configurations of the gas sensor cartridge and a non-volatile memory element provided inside thereof according to the present embodiment.

Alternatively, as illustrated in FIG. 22, for example, it is preferable to include a non-volatile memory element 43. The non-volatile memory element 43 is provided in the case 26 and connected to the external connection terminal 27, and the characteristics of the gas sensor device 6 are recorded in the non-volatile memory element 43.

For example, the non-volatile memory element 43 in which the characteristics of the gas sensor device 6 are recorded may be mounted on the substrate constituting the gas sensor device 6 provided inside the case 26 and this non-volatile memory element 43 may be connected to the external connection terminal 27.

In this case, for example, the non-volatile memory element 43 may preliminarily store information of: the basic characteristics of the gas sensor device 6; a conversion formula to convert response magnitude of the gas sensor device 6 into a gas concentration; a gas concentration measurement sequence; and the like. Then, every time the gas sensor device 6 is replaced, setting in the control unit 17 provided in the gas sensor body 20 may be reset by reading such stored information.

Furthermore, for example, replacement timing and the like may be determined by using the number of times of use of the gas sensor 5 recorded in the non-volatile memory element 43 through the external connection terminal 27. For example, a notice of replacement timing may be issued in accordance with the number of times of use of the gas sensor 5, thereby achieving improvement of convenience.

By the way, as for the gas sensor device 6 provided in the gas sensor cartridge 1 having the configuration as described above, the gas sensor device 6 may include at least one of: a gas sensitive material including oxide containing Sn, W, Zn, or In or any combination thereof as a main material; a gas sensitive material including a semiconductor containing C as a main material; or a gas sensitive material containing a halogen compound or oxide containing Cu or Ag as a main material.

With the use of such a gas sensitive material, a gas species containing, for example, any one of ammonia, hydrogen, acetone, ethanol, acetaldehyde, hydrogen sulfide, and carbon monoxide may be detected, and a concentration thereof may be measured.

In a case of using the gas sensitive material including the oxide containing Sn, W, Zn, or In or any combination thereof as the main material or the gas sensitive material including the semiconductor containing C as the main material (first gas sensitive material) out of the above-mentioned gas sensitive materials, the gas sensitive material may be provided at least between a pair of metal electrodes apart from each other and the gas sensitive material may be made to contact a heater via an insulation layer.

The first gas sensitive material includes tin oxide as an example.

Gas molecules and oxygen are heated by the heater, and an adsorption amount of active oxygen to the gas sensitive material is detected from a resistance change of the semiconductor material.

Selectivity (a difference in response intensity depending on each gas species) may be obtained by methods like selecting a kind of main metal, containing a noble metal having gas catalytic action, adjusting a heat amount of the heater, and the like.

A selection ratio between gas species may be acquired by containing additive metal such as palladium or platinum which is the noble metal, aluminum, lead, or the like.

For example, sensitivity to a gas to be detected is generally approximately 0.1 to 10 times that of acetone or ethanol, but the sensitivity is desirably higher than that.

Furthermore, an organic thin film may be formed in a manner laminated on the gas sensitive material in order to make a sensitivity difference from a volatile organic compound (VOC), for example.

In this case, it is desirable to form the film as thin as possible in order to relatively decrease the sensitivity.

For example, a monomolecular layer may be formed by coating a surface of oxide (here, tin oxide) with gold particles and exposing the surface to a polymer gas. For example, an amine-based, thiol-based, or silane-based coupling material may be used.

In this case, the gas sensor device 6 provided in the gas sensor 5 (metal oxide semiconductor sensor) is an example of a semiconductor gas sensor that has a configuration including a first gas sensitive material such as tin oxide or the like, the heater, and a detection electrode. The semiconductor gas sensor detects a gas concentration on the basis of a resistance value between the heater and the detection electrode.

Such a gas sensor 5 has an optimum detection temperature in accordance with a species of the gas to be detected, and the metal oxide semiconductor sensor (gas sensor device) is set to the optimum detection temperature during the gas concentration measurement in which gas detection is performed.

Alternatively, the gas sensor device is used after being heated to a detection temperature within a detection temperature range including the optimum detection temperature.

On the other hand, when the metal oxide semiconductor sensor (gas sensor device) is cleaned, contaminated substances adsorbed to a surface of the metal oxide semiconductor sensor is desorbed by heating the metal oxide semiconductor sensor up to a cleaning temperature higher than the detection temperature of performing the gas detection.

Furthermore, in a case of using a gas sensitive material including a halogen compound or oxide containing Cu or Ag as a main material (second gas sensitive material), the gas sensitive material at least between the pair of metal electrodes apart from each other may be provided.

The second gas sensitive material includes, as an example, copper(I) bromide (CuBr) that is a p-type semiconductor.

Since a nitrogen atom of ammonia can form a coordination linkage with a copper ion, the nitrogen atom has a strong adsorption property in a state in which an amino group is oriented to a CuBr surface.

In this case, heating by a heater may not be necessary because adsorption of gas molecules is utilized. However, it may be possible to improve sensitivity and responsiveness by lowering a temperature at the time of adsorption and increasing the temperature at the time of desorption by using the heater.

Furthermore, an organic thin film may also be formed in a manner laminated on the gas sensitive material in order to make a sensitivity difference, for example, relative to the volatile organic compound (VOC).

In this case, it is desirable to form the film as thin as possible in order to relatively decrease the sensitivity.

For example, a monomolecular layer may be formed by coating a surface of the CuBr with gold particles and exposing the surface to a polymer gas. For example, an amine-based, thiol-based, or silane-based coupling material may be used.

Note that a plurality of gas sensitive materials may be used in arbitrary combination. For example, the first gas sensitive material described above may be provided and the second gas sensitive material described above may also be provided next thereto on the same substrate.

By the way, the reason for adopting the configuration as described above is as follows.

Total medical care expenditure tends to be increased year by year in this aging society that is accelerating more and more, and there is a social problem that the total medical expenditure has exceeded 40 trillion yen in year 2013 according to the Ministry of Health, Labor and Welfare statistics in year 2015.

Speaking of a kind of disease, a proportion of diseases caused by lifestyle habits, such as high blood pressure, diabetes, and cancer occupies top ranks high, and there is a growing need for early detection of such diseases caused by diseases associated with adult lifestyle habits.

Considering such backgrounds, research has been made on: breath analysis to examine, from a biogas, an index of a body state; and a diagnosis method using the breath analysis.

A breath of a human or an animal contains very low-concentration gases that have been obtained by gasifying, in the lungs, chemical substances contained in blood and releasing the gasified chemical substances. Some of these gases may have deep relations with biological activity and diseases.

For example, it is said that an ammonia gas contained in a human breath is associated with liver metabolism and pylori infection that is a risk factor for a gastric cancer. Furthermore, nonanal belonging to aldehydes is a substance that is a candidate of a lung cancer marker substance.

The breath analysis is aimed at detecting a specific substance effective for screening in order to improve the lifestyle habits and early detection of diseases by analyzing these gases with an easy-handling tool that may require only exhaling without distress of physical restraint and blood sampling.

However, a biogas contains a large variety of volatile gases (more than 200 kinds according to a theory). Most of biogases are reducing gases or organic molecules (hydrocarbons) and have similar chemical properties.

There are roughly two kinds of methods of analyzing such gas components.

One is a measuring method aimed at a specific gas species by using a large-scale analyzer represented by gas chromatography.

In this method, gas components can be analyzed in detail, but an expert needs to operate the analyzer and many hours are spent to obtain results, and furthermore, the analyzer is expensive and large-sized. From such points, this method is mainly used for a research purpose due to the heavy burden on examination.

The other is a method of analyzing a difference in a response pattern caused by each gas between gas sensor devices in an apparatus in which many of the gas sensor devices are integrated.

In this method, a time until analysis results are obtained is short and the apparatus is portable and easy to use. However, a sensitivity difference between the gas sensor devices is small and it is difficult to discriminate a specific gas from other gases. Therefore, it can be hardly said that this method is good enough for the breath analysis to examine an index of a body state.

Many gas sensors in related art adopt tin oxide as a base of the material. The heater heats gas molecules and oxygen, and an adsorption amount of active oxygen to a gas sensitive material is detected from resistance change of a semiconductor material.

In this case, selectivity (a difference in responsive intensity depending on each gas species) is obtained by the methods like selecting a kind of main metal, containing a noble metal having gas catalytic action, adjusting a heat amount of the heater, and the like.

However, in any case, it is general that a time until change of the characteristics and a life to deterioration are short (for example, half a year to two years) because the gas sensor is accompanied by chemical reactions on a semiconductor surface. When the gas sensor is used as a gas concentration measurement system, there are many cases of adopting a system in which a sensor unit including a gas sensor device is replaced.

The sensor unit for replacement is normally retained airtighty in most cases, but since the sensor unit is an open system, the characteristics of the gas sensor device are fluctuated depending on, for example, retaining conditions and use conditions.

Therefore, even when an initial value is preliminarily stored, it may difficult to avoid increase in an error caused by fluctuation of the characteristics of the gas sensor device.

Furthermore, calibration is often performed by an expert at the time of replacement, and this may be a large burden on a user in an aspect of costs for calibration, replacement, and the like, and inhibits prevalence of the gas sensor system.

Considering the above, the configuration as described above is adopted.

Accordingly, the gas sensor and the gas sensor cartridge according to the present embodiment have an effect of reducing fluctuations in the characteristics (for example, initial characteristics) of the gas sensor device 6.

For example, the gas sensor device 6 is built inside the gas sensor cartridge 1 provided with airtightness and having set values preliminarily entered, and deterioration of a replacement component may be suppressed.

Furthermore, adjustment is not required thereafter, and even a user who is a non-expert may be able to easily and simply perform the replacement. Therefore, a user cost may be cut down.

Furthermore, as described above, when the gas sensor cartridge 1 is detached from the gas sensor body 20, the intake port 24 and the exhaust port 25 of the gas sensor cartridge 1 are sealed again with the first sealing member 28 and the second sealing member 29. Therefore, the way of use is not limited to replacement when deteriorated or when a life end has come like the related art but may include repeated use by performing the attachment/detachment.

By the way, in the gas sensor 5 having the configuration as described above, it is preferable that the gas sensor 5 that measures a concentration of ammonia is formed by using CuBr having the photocatalytic property for the sensitive film 9 (gas sensitive material) provided in the gas sensor device 6.

Here, CuBr having the photocatalytic property is a photocatalyst that contains cuprous bromide (CuBr) and exhibits the photocatalytic property of decomposing a substance that contacts CuBr by irradiating CuBr with light. In this case, the photocatalytic material is CuBr.

Here, CuBr is an ionic crystal containing monovalent copper and monovalent bromine, and is a polycrystalline body containing at least a (111)-oriented component.

This is based on a discovery that CuBr has the photocatalytic property as described below, and a photocatalyst containing CuBr is a new photocatalyst, and CuBr is a new photocatalytic material.

A developing mechanism of the photocatalytic property is considered as follows.

When a valence band and a conduction band absorb light energy having a wavelength corresponding to a bandgap between the valence band and the conduction band, electrons in the valence band are moved to the conduction band by excitation, and electron holes are generated in the valence band.

In the conduction band, the electrons that have been moved to the conduction band are moved to an organic substance and reduce the organic substance while assuming that some substance (for example, the organic substance) is adsorbed to a surface of a substance. In the valence band, the electron holes generated therein catch the electrons and oxidize the organic substance.

For example, since the electron holes of the valence band have significantly strong oxidizing power, titanium oxide finally decomposes the organic substances into water and carbon dioxide.

For example, the photocatalytic material is to be a material that has a bandgap corresponding to energy of irradiation light (for example, ultraviolet (UV)), has long lives of the generated electrons/electron holes, and also has strong oxidizing power/reducing power.

The present Inventor confirmed that CuBr had the photocatalytic property as follows.

The present inventor discovered the photocatalytic property of CuBr during other experiments from a fact that sensor resistance had dropped only at the time of UV irradiation.

Accordingly, the present inventor evaluated photocatalytic activity another time by a method described below, and confirmed that CuBr had the photocatalytic property.

First, a wavelength of the light (UV) for developing the photocatalytic property was calculated as follows.

Since a bandgap of CuBr has Eg=3.1 eV (see, for example, pp 63-66 of Materials Letter, 111 in "Deposition of earth-abundant p-type CuBr films with high hole conductivity and realization of p-CuBr/n-Si heterojunction solar cell" (2013) by K. V. Rajani, S. Daniels, M. Rahman, A. Cowley, P. J. McNally), the wavelength was calculated as λ=405 nm by plugging this value into Expression (1) below.

[Expression 1]

$$E = h\nu = \frac{hC}{\lambda} = \frac{1240}{\lambda} \quad (1)$$

Therefore, CuBr can develop the photocatalytic property by irradiating CuBr with light having the wavelength of 405 nm (UV; near UV).

From this fact, it was found that a light source including a component having the wavelength of 405 nm in the following evaluation may be used.

First, the photocatalytic property was confirmed by evaluation of JIS R 1701-2, for example, by a test of JIS R 1701-2.

Figure 23:
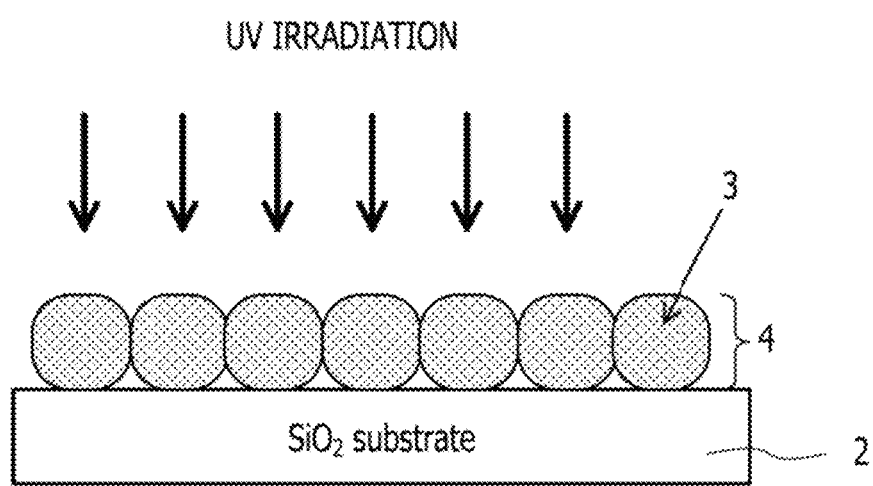
FIG. 23 is a schematic diagram illustrating a cuprous bromide (CuBr) film having a photocatalytic property and used for the gas sensor device provided in the gas sensor cartridge according to the present embodiment.

As illustrated in FIG. 23, a sample obtained by depositing a CuBr film (CuBr thin film) 4 containing CuBr crystal grains 3 was set on an Si substrate 2 including a $SiO_2$ film inside a hermetically-sealed desiccator, and then acetaldehyde ($CH_3CHO$) vapor was introduced until a gas phase concentration became about 10,000 ppm, and the sample was left for about one hour.

During this time, the desiccator was shielded so as not to allow external light to enter.

Subsequently, as illustrated in FIG. 23, the UV having a light amount of about 3 mW/cm² and a central wavelength of about 360 nm was emitted for about four hours (UV irradiation) from above the desiccator, and a concentration of carbon dioxide ($CO_2$) generated by an acetaldehyde gas and decomposition thereof inside the desiccator was measured by gas chromatography.

Figure 24A:
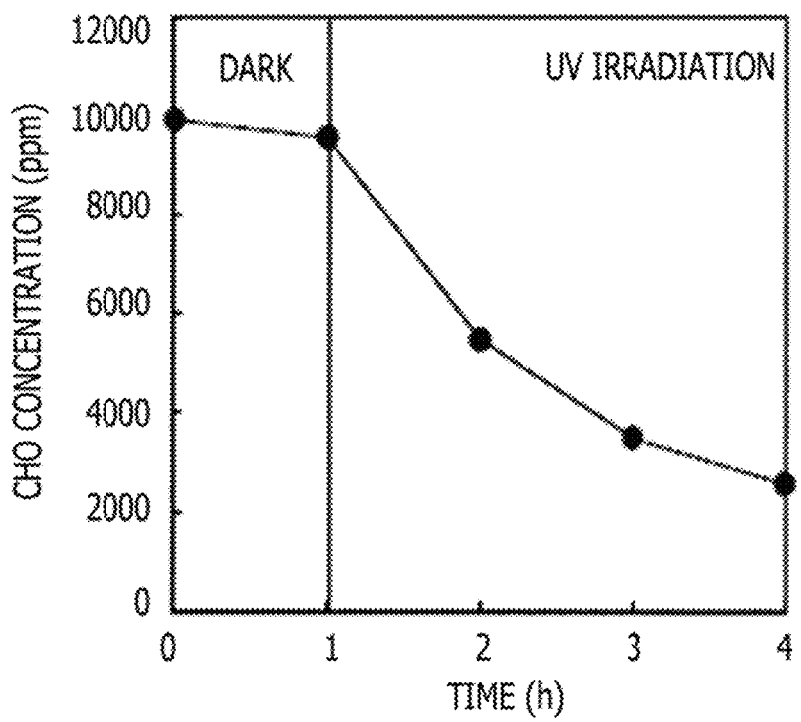
FIGS. 24A and 24B are charts illustrating results obtained by confirming a photocatalytic property in a JIS R 1701-2 test with respect to the CuBr film having the photocatalytic property and used for the gas sensor device provided in the gas sensor cartridge according to the present embodiment.
Figure 24B:
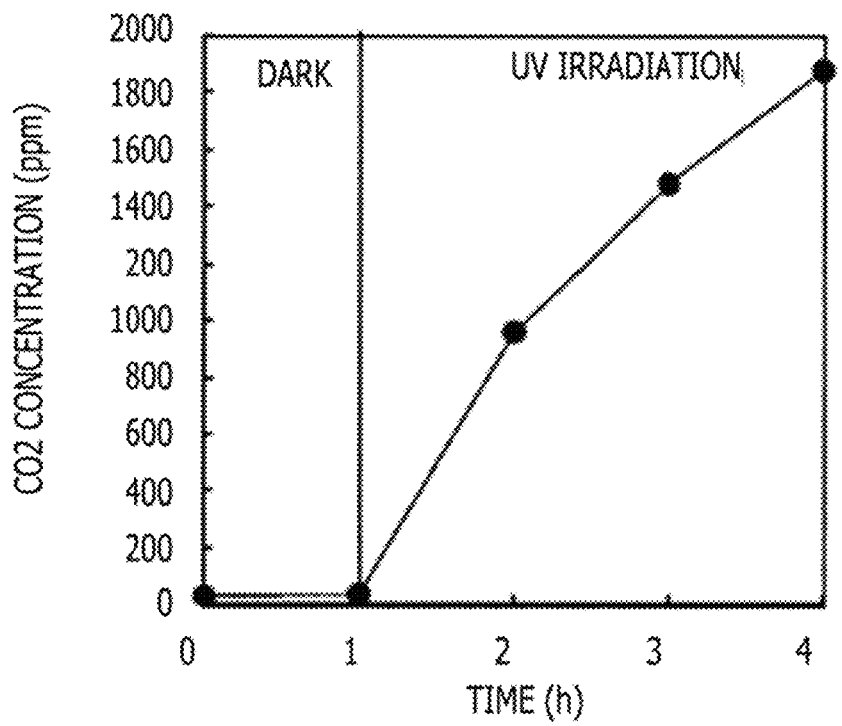

Here, FIGS. 24A and 24B illustrate results thereof.

As illustrated in FIG. 24A, it was found that the concentration of the acetaldehyde gas was rapidly decreased after starting the UV irradiation, and became approximately ¼ about four hours later.

On the other hand, as illustrated in FIG. 24B, it was found that the carbon dioxide is rapidly increased in synchronization with the UV irradiation.

This represented that the acetaldehyde filled inside the hermetically-sealed desiccator had been decomposed into carbon dioxide.

Consequently, it was surely confirmed that CuBr had the photocatalytic property.

Note that it could be considered that a reason why the gas concentration of the acetaldehyde was slightly decreased during a dark period before the UV irradiation was that the acetaldehyde was adsorbed to a chamber inner wall.

Next, evaluation by surface analysis, for example, X-ray photoelectron spectroscopy (XPS) analysis was conducted for a surface of the CuBr film 4 in a case of performing irradiation with the near UV and in a case of not executing the irradiation with the near V.

To assure the catalytic property, it may be necessary that the material itself is not changed before and after reaction.

For example, to confirm the photocatalytic property, it is necessary to confirm that compositions of the CuBr film 4 are not changed when comparison is made between before and after the UV irradiation.

To confirm a change in the surface of the CuBr film 4 caused by the WV irradiation (near UV irradiation), a surface of a sample (#75C3) obtained by irradiating the CuBr thin film 4 with LED UV (having the center wavelength of 405 nm) eleven times for about 10 seconds and a surface of a sample (#75D3) obtained by not performing the irradiation with the LED UV were each analyzed by the XPS, and the compositions thereof were compared.

Figure 25A:
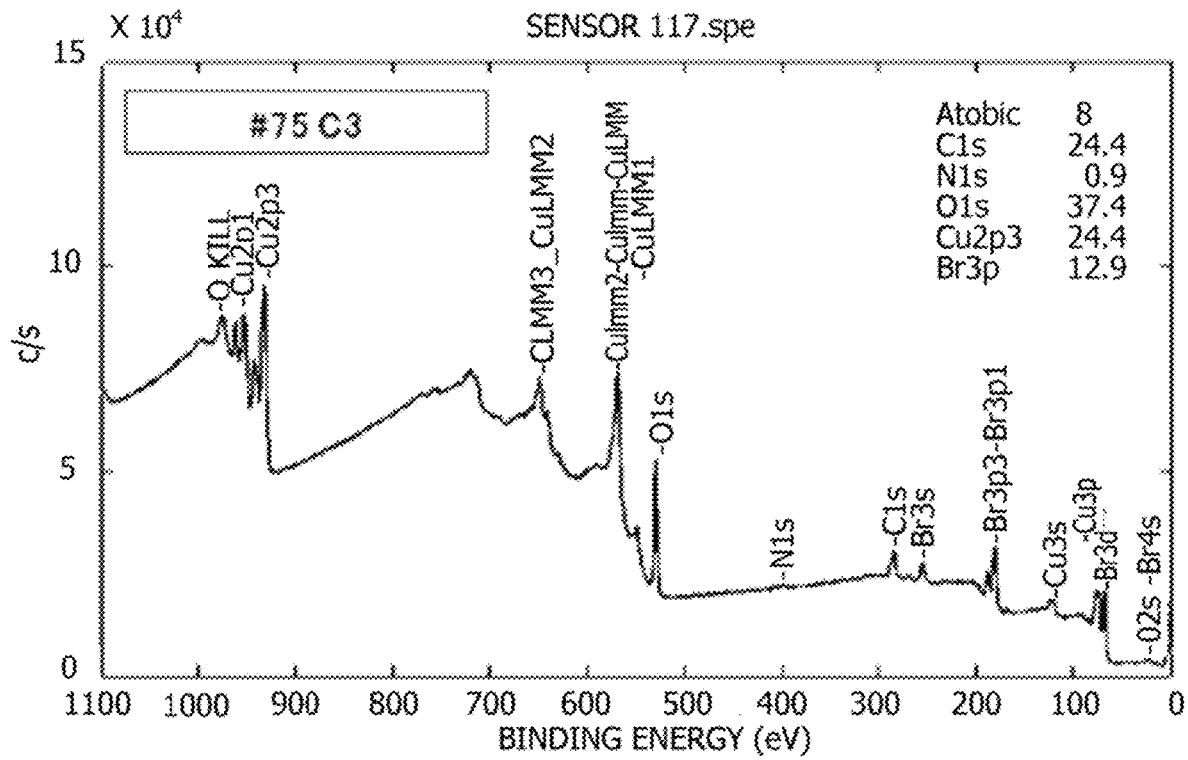
FIGS. 25A and 25B are charts illustrating results obtained by conducting X-ray photoelectron spectroscopy (XPS) analysis on a surface in a case of emitting near ultraviolet (near UV) and in a case of not emitting the near UV to the CuBr film having the photocatalytic property and used for the gas sensor device provided in the gas sensor cartridge according to the present embodiment.
Figure 25B:
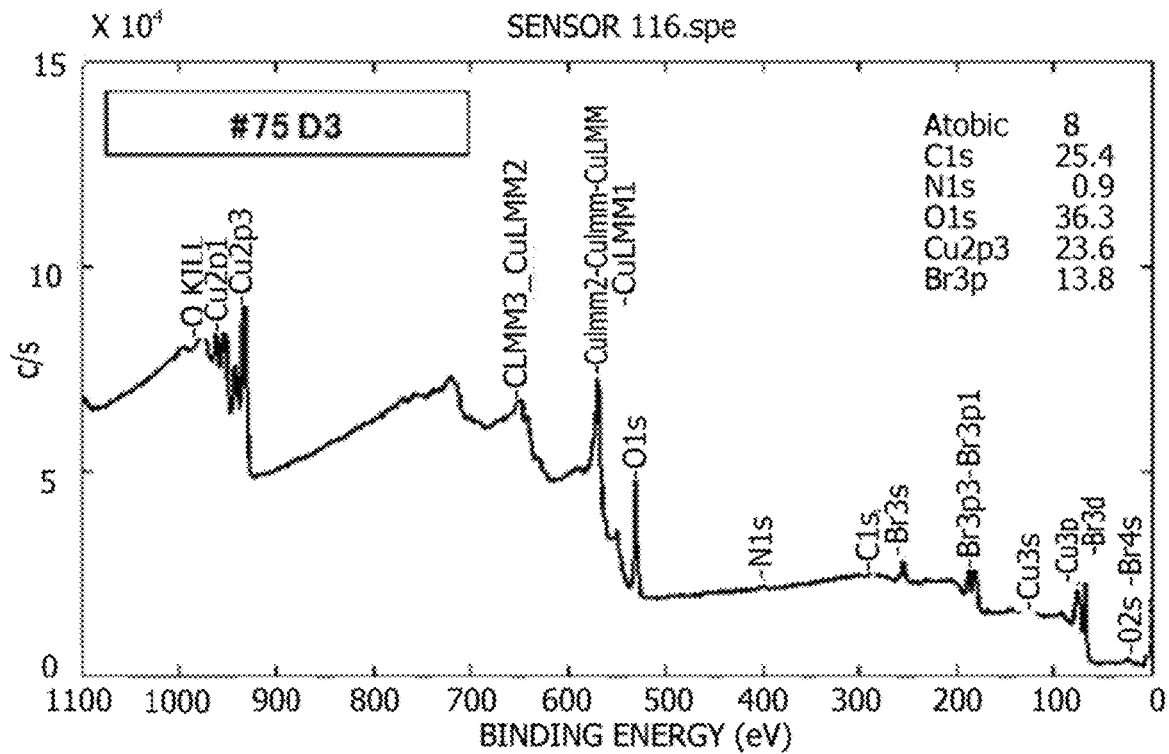

Here, FIGS. 25A and 25B illustrate results thereof.

Note that quantitative analysis results are illustrated in upper right in each of FIGS. 25A and 25B.

As illustrated in FIGS. 25A and 25B, elements detected in the sample irradiated with the UV and the sample not irradiated with the UV were C, N, O, Cu, and Br, and elements other than these were not detected. There was no difference in respective composition ratios between before and after the V irradiation.

Therefore, it could be considered that the compositions of the surface of the CuBr film 4 had not been changed before and after the UV irradiation, and it could be confirmed that CuBr surely functioned as a catalyst.

Thus, it was possible to confirm, from the above-described two kinds of evaluation, the fact that CuBr had the photocatalytic property.

The light required for developing the photocatalytic activity of CuBr is not particularly limited as far as the light has a wavelength of about 410 nm or less, and may be appropriately selected in accordance with a purpose.

For example, the photocatalytic property of CuBr can be developed by emitting the light (UV) including UV, preferably, emitting the light (near UV) including near UV.

Here, the UV is the light having a wavelength of about 10 nm to about 410 nm, and the near UV is the light having a wavelength of about 320 nm to about 410 nm.

Considering a cost for a light source and the like, the irradiation with the near UV having a wavelength from about 380 nm to about 410 nm is preferable.

For example, use of the UV-LED may achieve advantages such as a compact size, light weight, a low cost, safety, easy handling, and the like.

Note that what decomposed by the photocatalytic property of CuBr is not particularly limited and may be appropriately selected in accordance with a purpose.

Figure 26:
FIG. 26 is a diagram illustrating examples of decomposition of $NH_3$ by CuBr having the photocatalytic property and used for the gas sensor device provided in the gas sensor cartridge according to the present embodiment.
Figure 26:
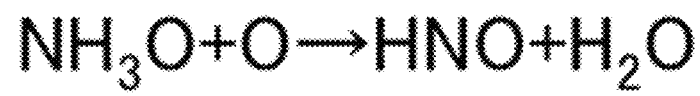
Figure 26:
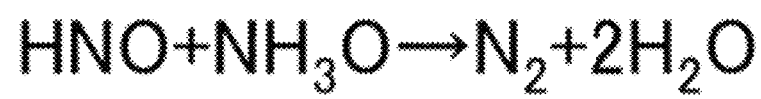
Figure 26:
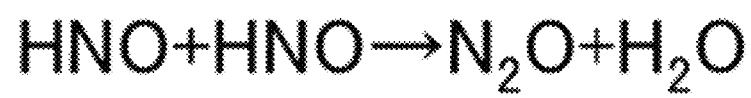

For example, as exemplary components thereof, it is reported that not only organic substances such as proteins, amino acids, lipids, sugars, and the like but also a specific inorganic substance, for example, $NH_3$ is decomposed (for example, see FIG. 26; and see pp. 2251-2255 of "$NH_3$ Oxidation over UV-Irradiated $TiO_2$ at Room Temperature" by H. Mozzanega et al. in *The Journal of Physical Cemistry*, Vol. 83, No. 17, 1979).

By the way, CuBr has the photocatalytic property as described above, whereas CuBr also has a gas sensitive property to serve as a sensitive film of a gas sensor having characteristics of high sensitivity and high selectivity to the ammonia gas (for example, see "*Development of Portable Breath Sensor for Measuring Ammonia Component in Breath in Short Time*" by Michio USHIGOME, Kazuaki KARASAWA, Satoru MOMOSE, Ryozo TAKASU, and Osamu TSUBOI, and also see "*Sensor Micromachine and Application System*" in the 33rd Symposium Abstracts, 25am2-PS-079, (2016)) by the Institute of Electrical Engineers of Japan.

Utilizing these two properties, an ammonia gas sensor is formed by using CuBr having the above-described photocatalytic property. Consequently, a gas sensor that shortens a measurement time (a time required for measurement; here mainly a recovery time) may be implemented.

Note that, not limited thereto, CuBr having the above-described photocatalytic property may also be used as a gas sensor other than the ammonia gas sensor.

In this case, as illustrated in FIG. 29, the gas sensor device 6 provided in the gas sensor 5 may include the first electrode 7, the second electrode 8, and the sensitive film 9 connecting the first electrode 7 and the second electrode 8; and the sensitive film 9 may contain CuBr and exhibit the photocatalytic property of decomposing a substance that contacts CuBr by irradiating CuBr with the light.

In this case, the sensitive film 9 is a CuBr film. Furthermore, the gas sensor device 6 is also referred to as a CuBr sensor device. Furthermore, the first electrode 7 and the second electrode 8 are, for example, Au electrodes.

Additionally, the gas sensor 5 may include: the gas sensor device 6 having such a configuration; and the light source 10 that irradiates the sensitive film 9 of the gas sensor device 6 with the light.

Here, as the light source 10, a light source that emits light including a wavelength component in a UV region (near UV region), for example, the UV-LED may be used.

For example, the thin film (CuBr film; CuBr thin film) 9 containing CuBr is formed in a manner stretching over the two Au electrodes (the first electrode 7 and the second electrode 8) formed on the substrate 11 including an Si thermal oxide film, in which CuBr exhibits the photocatalytic property of decomposing, by light irradiation, a substance that contacts the CuBr, and may be used as the gas sensor device that is the sensitive film 9 to the ammonia gas.

Additionally, the gas sensor 5 may include: the gas sensor device 6 having such a configuration; and a light irradiation mechanism that irradiates a surface of the sensitive film with light having a wavelength required to develop a photocatalytic function (here, an UV irradiation mechanism; the light source 10; for example, the UV-LED).

For example, in a gas sensor in the related art that does not include the light source 10 like the UV-LED but includes the CuBr sensor device 6, a gas concentration is measured by exposing the gas sensor device 6 to a gas to be measured, the switch to clean air is performed as preparation of next measurement, and initialization is performed by returning increased resistance (sensor resistance) of the gas sensor device 6 to original resistance.

For example, when the gas sensor device 6 is exposed to the gas to be measured, gas molecules are adsorbed to the surface of the sensitive film (CuBr film) 9 of the gas sensor device 6. Therefore, after measuring the gas concentration in this state, the state is returned to an original state by introducing the dean air (purge gas) and desorbing the gas molecules from the surface of the sensitive film 9 (see FIG. 28, for example).

Figure 27:
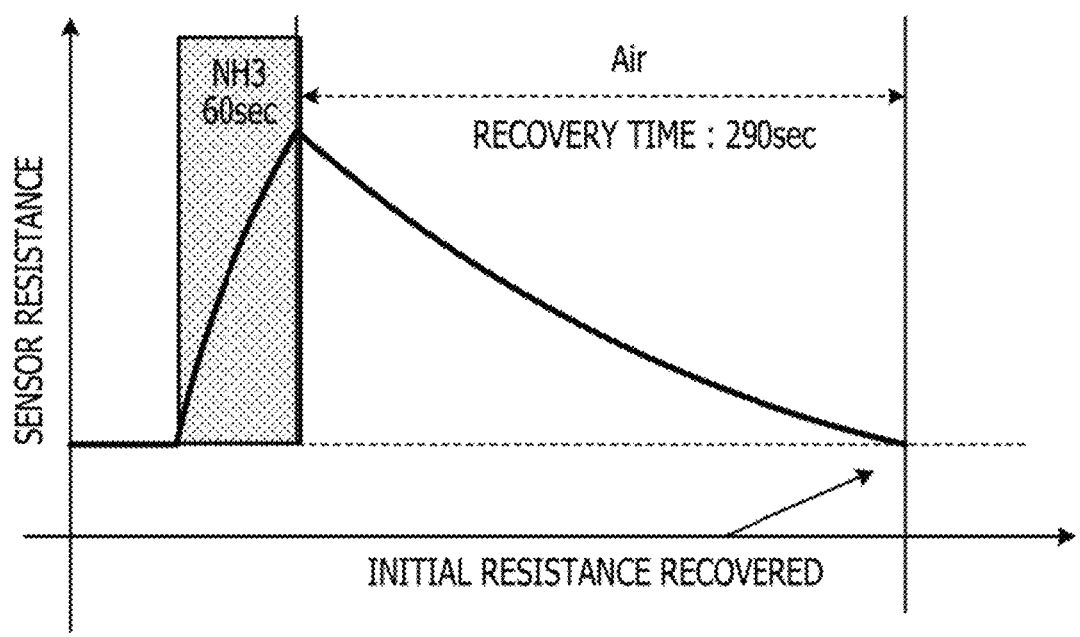
FIG. 27 is a chart illustrating exemplary changes in sensor resistance at the time of a gas response and at the time of recovery in a gas sensor in related art not including a light source.
Figure 28:
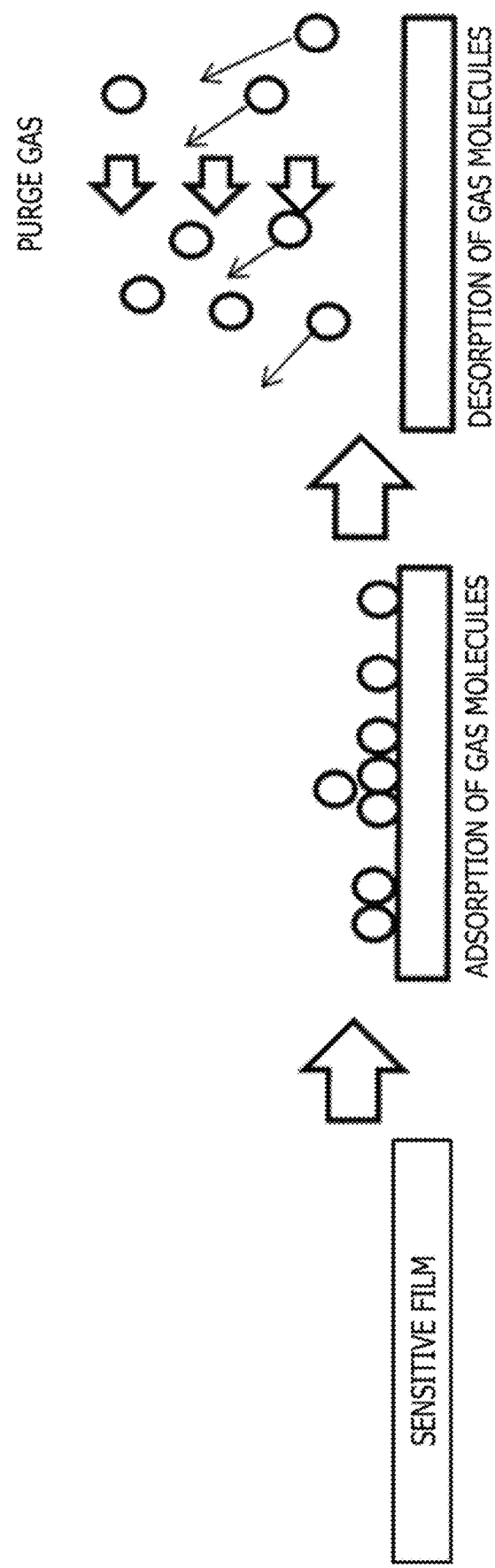
FIG. 28 is a diagram illustrating adsorption and desorption of gas molecules relative to a sensitive film at the time of gas response and at the time of recovery in the gas sensor.

Here, FIG. 27 illustrates exemplary changes in sensor resistance in the gas sensor in the related art that does not include the light source 10 like the UV-LED but includes the CuBr sensor device 6, for example.

As illustrated in FIG. 27, a measurement time of the ammonia gas (ammonia gas exposure time) is about 60 seconds, whereas a recovery time until initial resistance is recovered by introducing the clean air (air) is about 290 seconds, in which the recovery time is about 5 times longer than the measurement time (ammonia gas exposure time).

Figure 30:
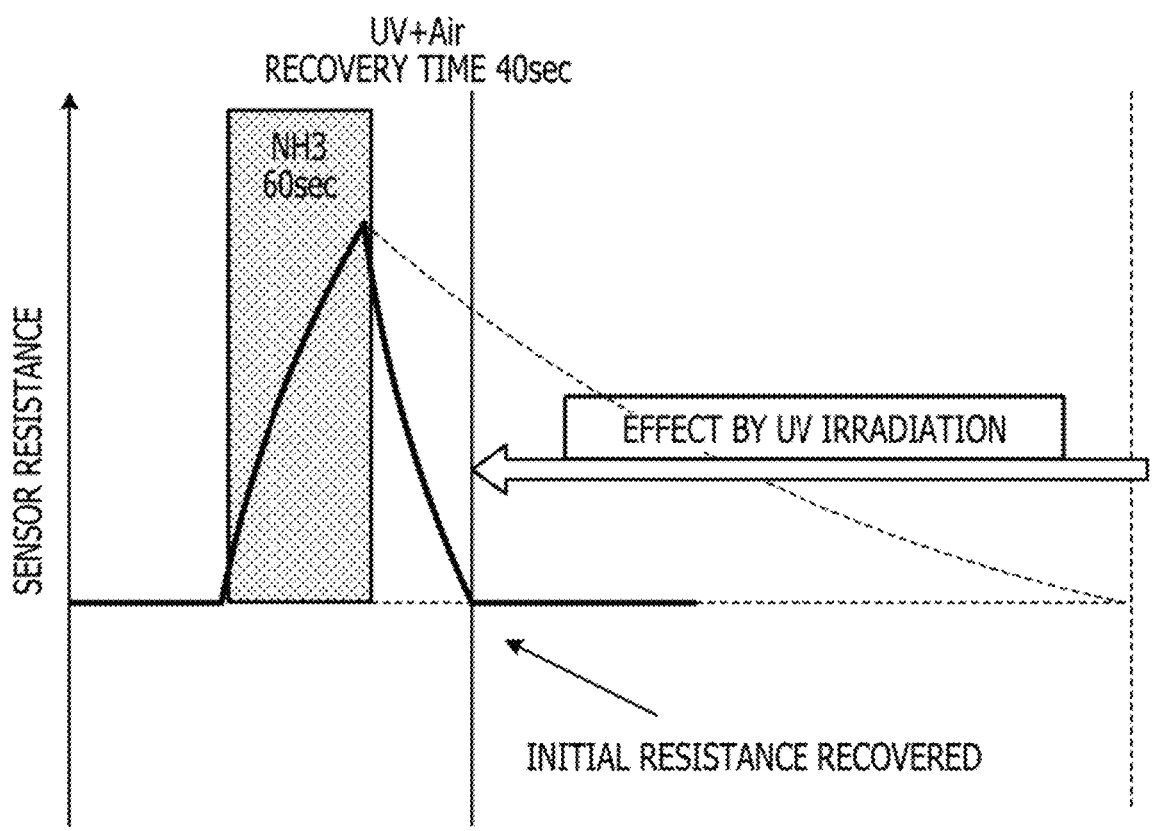
FIG. 30 is a chart illustrating exemplary changes in sensor resistance at the time of gas response and at the time of recovery in the gas sensor according to the present embodiment.

On the other hand, when the UV irradiation mechanism (the light source 10; here, the UV-LED) is installed immediately above the sensitive film 9 of the gas sensor device 6 as described above (see FIG. 29, for example), the changes in the sensor resistance result becomes as illustrated in FIG. 30 as an example.

As illustrated in FIG. 30, the recovery time is changed from about 290 seconds to about 40 seconds, which is about ⅐, and the recovery may be performed in a time shorter than the measurement time of the ammonia gas (ammonia gas exposure time; here, about 60 seconds).

Furthermore, the initialization is performed by spontaneously desorbing the gas molecules adhering to the surface of the sensitive film 9 (the film including the gas sensitive material; here, the CuBr film) of the gas sensor device 6 by introducing the dean air.

On the other hand, in the present embodiment, the gas molecules are forcibly decomposed and desorbed by emitting the UV. Therefore, there may be no need to introduce the dean air by using a filter or the like, and for example, it is preferable just to introduce the outside air without using any filter.

Note that the gas molecules can be desorbed by emitting the UV, but it is preferable to introduce the dean air or the outside air so as to suppress re-adsorption.

Figure 31:
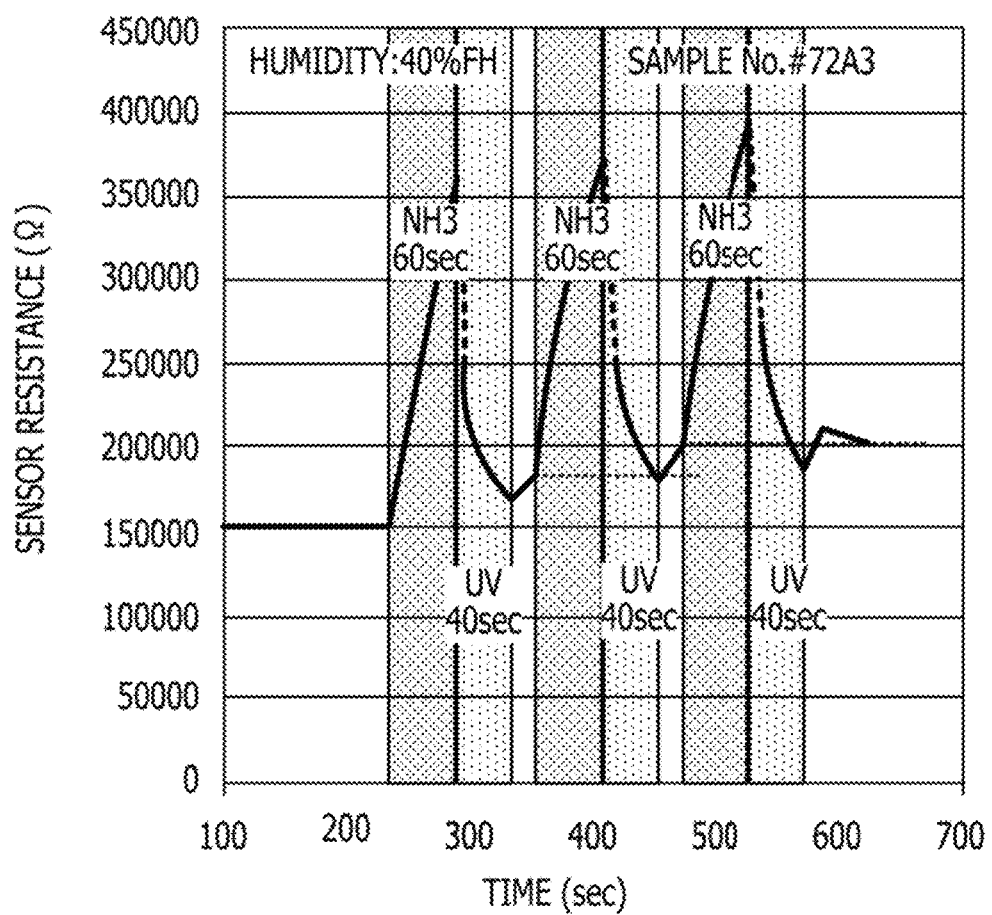
FIG. 31 is a chart illustrating results obtained by actually measuring a gas concentration by using the gas sensor according to the present embodiment.

Here, FIG. 31 illustrates an example in which a concentration of an ammonia gas was actually measured consecutively three times.

Since the configuration as described above was provided and the recovery time could be shortened by performing the UV irradiation during the recovery time, it was possible to consecutively measure the concentration of the ammonia gas as illustrated in FIG. 31.

In the above, the UV irradiation (preferably, the near UV irradiation) is used to shorten the recovery time of the gas sensor, but not limited thereto, and the UV irradiation (preferably, the near UV irradiation) may also be used to recover sensitivity of the gas sensor device 6 in which the surface of the sensitive film 9 is contaminated and the sensitivity is degraded.

Consequently, it may be also possible to extend the life of the gas sensor 5 (gas sensor device 6).

Figure 32:
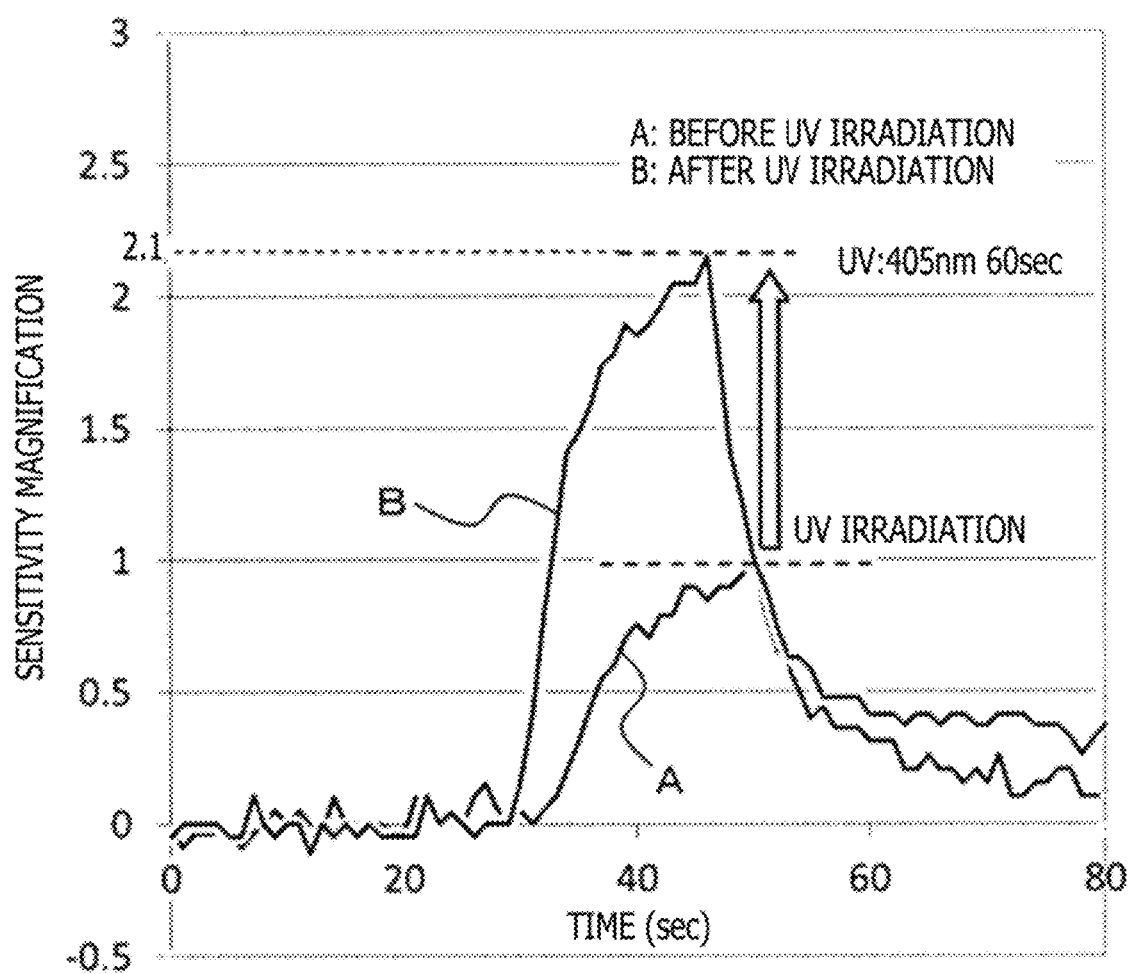
FIG. 32 is a chart illustrating a fact that a response property is recovered by irradiating the sensitive film including CuBr with ultraviolet (UV) in the gas sensor according to the present embodiment.

Here, FIG. 32 is a chart illustrating results of confirming response to the ammonia gas by performing the UV irradiation for the gas sensor device 6 manufactured two or more years ago and having degraded response to the ammonia gas.

As illustrated in FIG. 32, it is found that the response to the ammonia gas after the UV irradiation is about double the response before the UV irradiation.

It is considered that the sensitivity is recovered to some extent by decomposing and volatilizing, by the UV irradiation, organic substances and amine-based substances accumulated on the surface of the sensitive film (CuBr film) 9 for a long time.

Here, FIG. 33 illustrates an example of the gas sensor 5 using a UV-LED 10 as a near UV light source.

Note that the gas sensor 5 is also referred as a gas sensor system. Furthermore, in FIG. 33, a solid line represents gas pipe line, and a broken line represents an electric signal path.

As illustrated in FIG. 33, the gas sensor 5 includes the gas sensor device 6 having the configuration as described above, the UV-LED (light source) 10, the gas supply-side pipe 12, the solenoid valve 13 provided in the gas supply-side pipe 12, the filter 14 provided in the gas supply-side pipe 12, the exhaust-side pipe 15, the pump 16 provided in the exhaust-side pipe 15, and the control unit 17. Note that the communication unit 19, the power source 23, the display unit, and the like are omitted here.

Here, the gas sensor device 6 is provided inside the sensor chamber 18. Additionally, the sensor chamber 18 includes the case 26 of the gas sensor cartridge 1 described above.

This gas sensor 5 has a structure in which the outside air is sucked to the vicinity of the gas sensor device 6 by the pump 16.

Furthermore, paths from a suction port (an introduction port; the inlet 21 of the gas sensor body 20) include, for example: a path passing through the filter 14 such as activated carbon or the like; and a path not passing through the filter 14, and provided is a structure in which switching between these paths is performed by the solenoid valve (a three-way solenoid valve) 13.

Note that the solenoid valve 13 is used here, but a valve to perform the switching between these paths is not limited to an electric valve, and a manual valve may also be used as far as a valve is able to switch the gas flow path.

Furthermore, a UV-LED (UV-LED unit) is installed as the UV light source (near UV light source) 10 immediately above the gas sensor device 6.

Note that the light source 10 may be a light source having a wavelength at which the sensitive film 9 (here, the CuBr film) of the gas sensor device 6 becomes photocatalytically active, and the light source 10 is not limited to the UV-LED. For example, in the case where the sensitive film 9 is a CuBr film, the light source may be able to emit light having a wavelength of about 410 nm or less.

Furthermore, the pump 16, the solenoid valve 13, and the UV-LED 10 are all connected to the control unit 17 so as to be controlled by the control unit 17 in accordance with a programmed sequence.

Furthermore, in a case of supplying the gas to be measured, a concentration of the gas to be measured is measured by the control unit 17 on the basis of a value detected by the gas sensor device 6.

Therefore, it is also possible to achieve the flexible gas sensor 5 by changing a sequence in accordance with, for example, a measurement target, a measurement environment, and a purpose.

Figure 34:
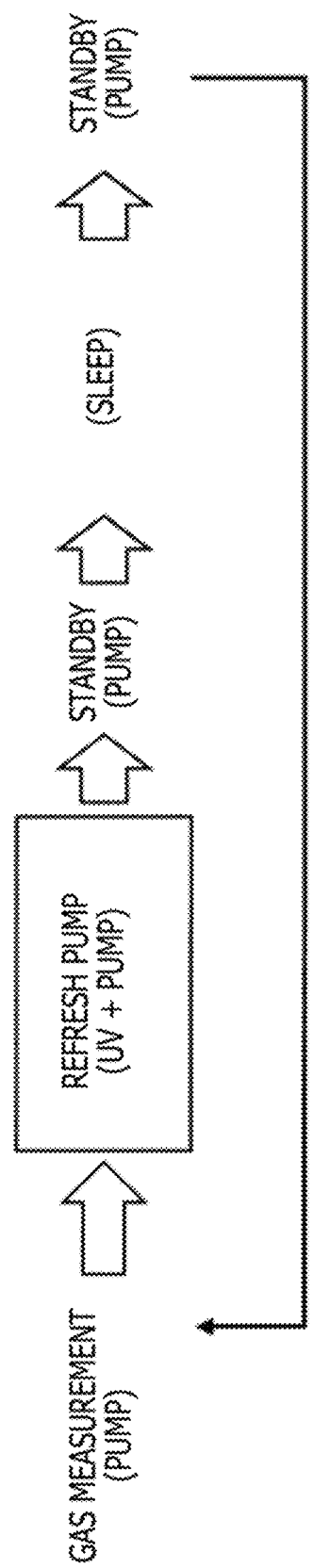
FIG. 34 is a diagram illustrating a gas concentration measurement sequence of the gas sensor according to the present embodiment.

Here, FIG. 34 illustrates an exemplary sequence of a gas sensor (gas concentration measurement sequence) capable of automatically and consecutively measuring a gas concentration.

As illustrated in FIG. 34, the pump 16 is started to take in the gas to be measured to the gas sensor device 6 having the configuration as described above.

First, in a gas measurement process, the pump 16 is activated to detect a change amount in resistance (sensor resistance) of the gas sensor device 6 for a certain time, and a gas concentration corresponding to the change is calculated.

Note that the gas concentration (data) thus calculated, a set value, a detection value, and the like may be displayed on the display unit, or may be transmitted by the communication unit to, for example, another terminal or a server.

Furthermore, correspondence relation data of the response of the gas sensor device 6 to the gas concentration is acquired in advance and stored in the memory inside the control unit 17.

Next, the path is switched to the filter 14 side by the solenoid valve 13 in a refresh (recovery) process while keeping the pump 16 activated, and the UV irradiation is performed in synchronization with introduction of the dean air.

Note that the dean air is taken in through the filter 14 here, but not limited thereto, and the outside air may be taken in not through the filter 14.

Such introduction of the clean air and the UV irradiation are performed until the gas sensor device 6 is recovered.

Figure 36:
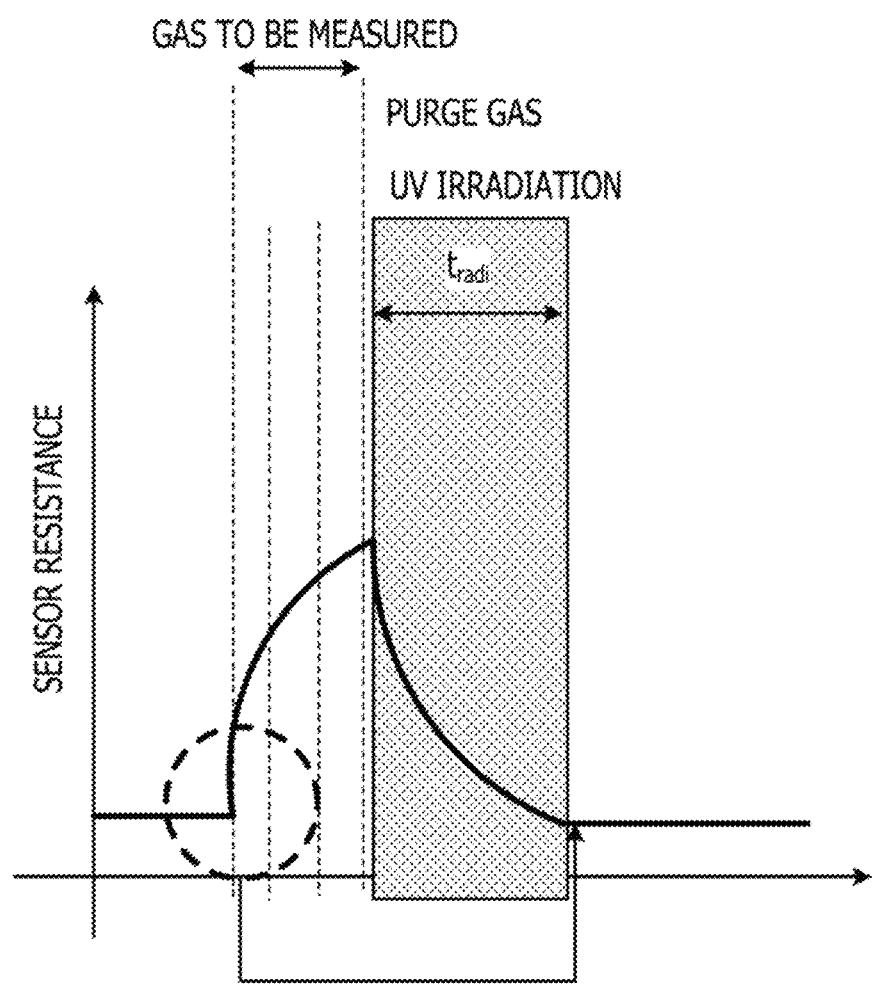
FIG. 36 is a diagram to describe control at the time of measuring the gas concentration and at the time of recovery in the gas sensor according to the present embodiment.

Here, since a time until the gas sensor device 6 is recovered has a relation with magnitude of the response of the gas sensor device 6, the sensor resistance is monitored also after the gas concentration measurement, and the time not to a fixed time but a time until the gas resistance is returned to gas resistance immediately before the gas concentration measurement may be set (see FIG. 36, for example).

Then, the refresh process is stopped (UV irradiation is stopped) at the timepoint at which the sensor resistance is returned to the sensor resistance immediately before the gas concentration measurement, and the pump 16 is kept activated and made standby.

Subsequently, in a case where there is next measurement, the measurement is repeated again.

In a case where there is no measurement soon, the pump 16 is stopped and made standby (sleep state).

Figure 35:
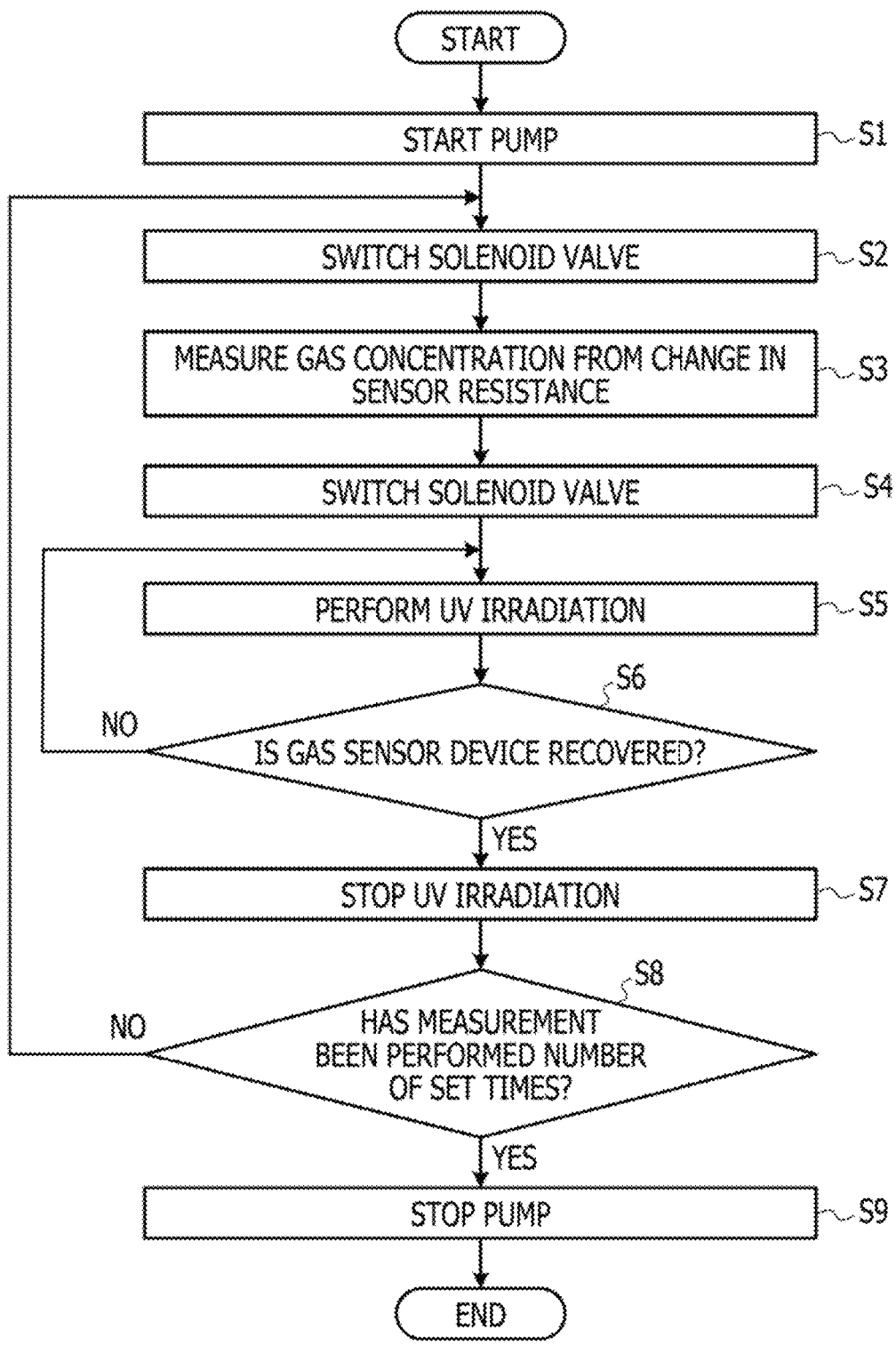
FIG. 35 is a flowchart to describe processing in the gas concentration measurement sequence of the gas sensor according to the present embodiment.

Here, FIG. 35 is a flowchart Illustrating processing (a measurement method) in a case where such a gas concentration measurement sequence is implemented when the control unit 17 provided in the gas sensor 5 executes a program.

As illustrated in FIG. 35, first of all, the control unit 17 controls the pump 16 to start the pump 16 (step S1).

Next, the control unit 17 controls the solenoid valve 13 to introduce a gas to be measured, and switches the path of the gas supply-side pipe 12 to the path not passing through the filter 14 (step S2).

Consequently, the gas to be measured is supplied into the sensor chamber 18 (the case 26 of the gas sensor cartridge 1) where the gas sensor device 6 having the configuration as described above is provided.

Next, the control unit 17 measures a concentration of the gas to be measured on the basis of a value detected by the gas sensor device 6 (step S3).

Here, the control unit 17 detects a change amount in resistance (sensor resistance) of the gas sensor device 6 for a predetermined time (a fixed time; 60 seconds, for example), and measures a concentration of the gas to be measured by calculating the gas concentration corresponding to the change.

For example, a resistance value from the gas sensor device 6 immediately before the gas sensor device 6 is exposed to the gas to be measured is preliminarily stored as an initial value, and the gas concentration at a timepoint of introducing the gas to be measured for a fixed time may be calculated on the basis of a change in the resistance value from the initial value of the resistance value from the gas sensor device 6.

For example, when a timepoint of starting measurement immediately before exposure to the gas to be measured is defined as 0 second, a sensor resistance value at this time is defined as R0, and a sensor resistance value after $t_{meas}$ seconds is defined as Rs, the gas concentration may be derived by calculating a change rate of the resistance value |R0−Rs|/R0−1 and plugging the calculated value into a gas concentration conversion formula stored in the memory or the like inside the control unit 17.

Thus, the control unit 17 measures the concentration of the gas to be measured on the basis of: the resistance value detected from the gas sensor device 6 at the time of starting supply of the gas to be measured; and the resistance value detected from the gas sensor device 6 at the time of having supplied the gas to be measured for the predetermined time.

Next, the control unit 17 controls the solenoid valve 13 to introduce dean air instead of the gas to be measured while keeping the pump 16 activated, and switches the path of the gas supply-side pipe 12 to the path passing through the filter 14 (step S4).

Consequently, the dean air is supplied into the sensor chamber 18 (the case 26 of the gas sensor cartridge 1) where the gas sensor device 6 is provided.

Note that the clean air is also referred to as a purge gas. Furthermore, a mechanism that thus supplies the purge gas instead of the gas to be measured is also referred to as a purge gas supply mechanism. Here, the purge gas supply mechanism includes the solenoid valve 13 and the filter 14.

Next, the control unit 17 controls the UV-LED (the light source 10; UV irradiation mechanism) to emit light having a wavelength necessary to develop the photocatalytic function, and performs UV irradiation for the sensitive film (here, the CuBr film; see FIG. 29) 9 of the gas sensor device 6 (step S5).

Thus, the UV irradiation is performed for the surface of the sensitive film 9 of the gas sensor device 6 during the recovery time in which the gas sensor device 6 is refreshed (recovered) after measuring the concentration of the gas to be measured. During the recovery period, the dean air is introduced to desorb the gases adsorbed onto the surface of the sensitive film 9 of the gas sensor device 6 (see FIG. 36, for example).

For example, the UV irradiation is performed for the surface of the sensitive film 9 of the gas sensor device 6 at the time of recovering the sensor resistance immediately after measuring the concentration of the gas to be measured.

In this case, the UV irradiation is performed for the surface of the sensitive film 9 of the gas sensor device 6 while supplying the dean air to the gas sensor device 6.

Next, the control unit 17 determines whether or not the gas sensor device 6 is recovered (step S6).

Here, the control unit 17 monitors the sensor resistance also after the gas concentration measurement, and determines whether or not the gas sensor device 6 is recovered in accordance with whether or not the sensor resistance is returned to the value immediately before the gas concentration measurement (the initial value stored at the beginning).

As a result of this determination, in a case of determining that the gas sensor device 6 is not recovered, the processing proceeds to a NO route and is returned to step S5 to continue the UV irradiation.

Consequently, the UV irradiation is started in synchronization with switching the gas to be supplied to the purge gas from the gas to be measured, and the UV irradiation is continued until the sensor resistance is recovered to the sensor resistance equal to or less than that immediately before introducing the gas to be measured (see FIG. 36, for example).

Then, in a case where the control unit 17 determines that the gas sensor device 6 is recovered, the processing proceeds to a YES route to stop the UV irradiation (step S7).

Here, since the UV irradiation is performed together with the introduction of the purge gas, a recovery time ($t_{radi}$) is shortened more than in a case of not performing the UV irradiation. The recovery time is, for example, about 290 seconds to about 40 seconds, which is about 1/7 (see FIG. 30, for example).

Consequently, the refresh process ends. However, note that the pump 16 becomes the standby state in which the clean air is kept flowing because the pump 16 is not stopped at this timepoint. At this time, the sensor resistance becomes a stable state while having the sensor resistance returned to the initial value.

Next, the control unit 17 determines whether or not measurement has been performed the number of set times (step S8).

As a result of this determination, in a case where the measurement has not been performed the number of set times, the processing proceeds to a NO route and is returned to step S2 to repeat the measurement.

Then, in the case where the control unit 17 determines that the measurement has been performed the number of set times, the processing proceeds to a YES route, and the control unit 17 controls the pump 16 to stop the pump 16 (step S9) and ends the processing.

Note that, here, the description has been provided for the exemplary case where the next measurement is performed while the pump 16 is activated and made standby after completion of the first measurement, but in a case where a time before starting the next measurement is long and the like, a sleep state in which the pump 16 is stopped and made standby may also be included.

Furthermore, for example, when a time sufficiently longer than a UV irradiation time has elapsed (for example, about 3 times the UV irradiation time), the pump 16 may be stopped.

Figure 37:
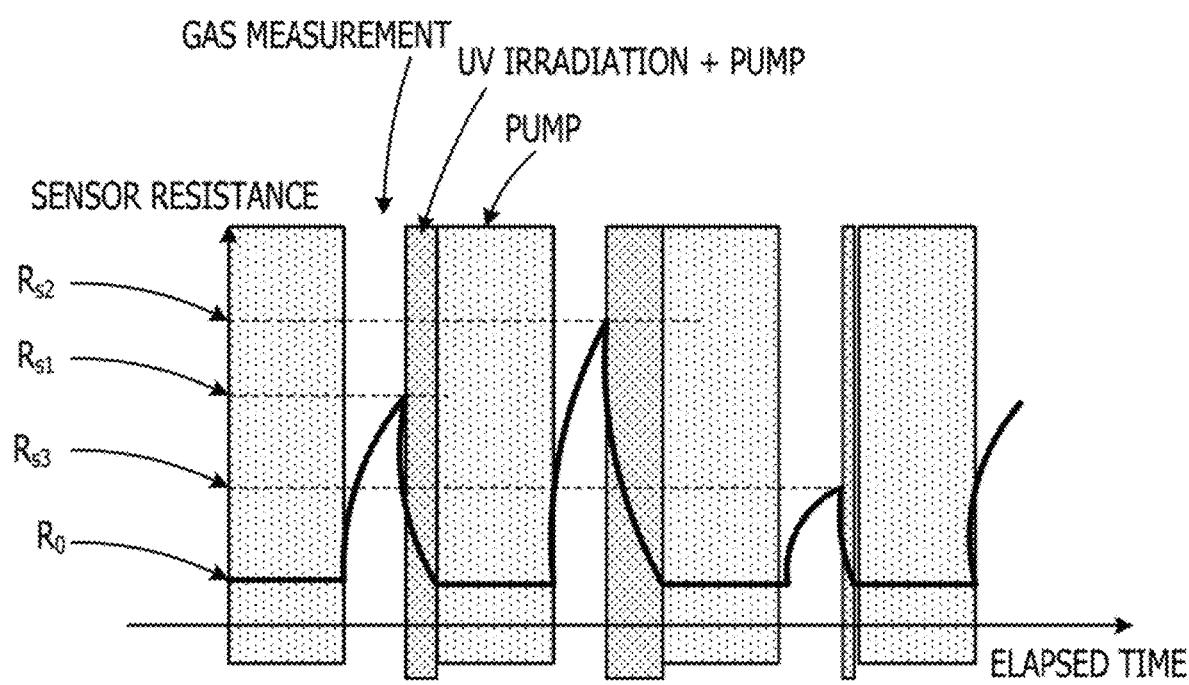
FIG. 37 is a diagram illustrating exemplary temporal changes in the sensor resistance in a case of measuring the gas concentration along the gas concentration measurement sequence in the gas sensor according to the present embodiment.
Figure 38:
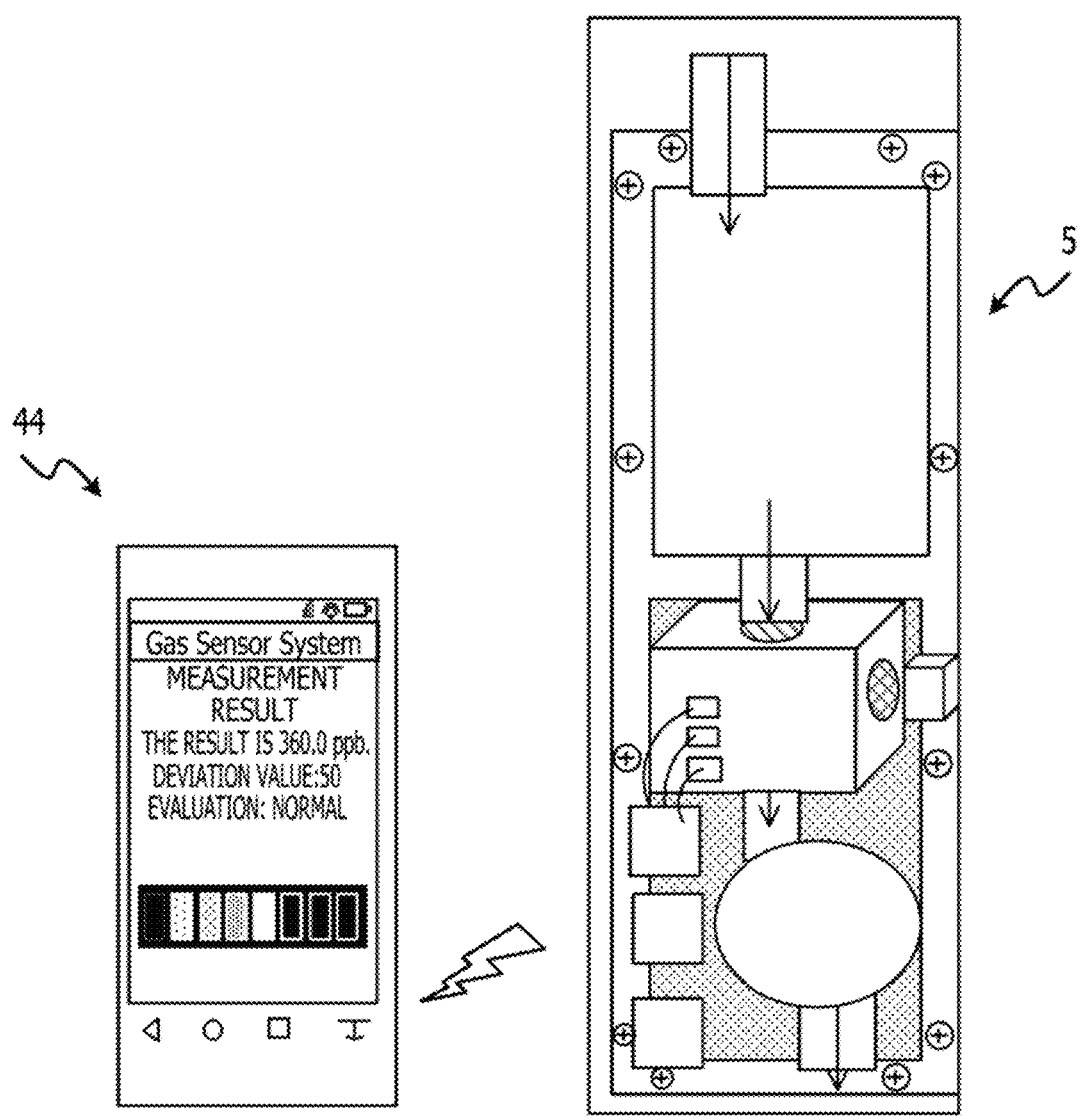
FIG. 38 is a diagram illustrating a configuration of a system including: a breath sensor to which the gas sensor according to the present embodiment is applied; and a terminal.

Here, for example, FIG. 37 illustrates exemplary temporal changes in the sensor resistance in a case of measuring a gas concentration as described above.

In the related art, it is difficult to consecutively measure a concentration because a relatively long time is required for recovery, whereas according to the present embodiment, the recovery time is shortened by performing the UV irradiation and it may become possible to perform the gas concentration measurement at short time intervals.

Thus, since the gas sensor 5 having the configuration as described above is made to include the UV Irradiation mechanism (UV irradiation optical system; the light source 10) as the refresh mechanism to refresh (recover) the gas sensor device 6 by irradiating the gas sensor device 6 with the light, it may be possible to shorten the recovery time (refresh time) and perform the gas concentration measurement at the short intervals.

Note that here the description has been provided for the exemplary case where the light irradiation mechanism (the UV irradiation mechanism; the light source 10) is provided as the refresh mechanism to refresh (recover) the gas sensor device 6 by irradiating the gas sensor device 6 with the light in the case of using the CuBr having the photocatalytic property for the sensitive film (gas sensitive material) 9 of the gas sensor device 6, but it is not limited thereto.

For example, even in a case where another gas sensitive material, for example, a gas sensitive material having no photocatalytic property is used for the sensitive film (gas sensitive material) 9 of the gas sensor device 6, there is a case where it may be preferable to provide the light irradiation mechanism (the UV irradiation mechanism; the light source 10) as the refresh mechanism to refresh (recover) the gas sensor device 6 by irradiating the gas sensor device 6 with the light.

For example, even in the case of using another gas sensitive material of the gas sensor device 6 and a gas sensitive material having no photocatalytic property, there is a case where gas molecules contacting the gas sensitive material due to adhesion, adsorption, and the like to the gas sensitive material may be able to be decomposed (directly decomposed) by emitting light while adjusting a wavelength and power of the light to be emitted.

In this case, it may be possible to refresh (recover) the gas sensor device 6 by providing the light irradiation mechanism (the UV irradiation mechanism; the light source 10) as the refresh mechanism to refresh (recover) the gas sensor device 6 by irradiating the gas sensor device 6 with light.

Therefore, even in a case where another gas sensitive material, for example, the gas sensitive material having no photocatalytic property is used for the gas sensitive material of the gas sensor device 6, there is a case where it may be preferable to provide the light irradiation mechanism (the UV irradiation mechanism; the light source 10) as the refresh mechanism to refresh (recover) the gas sensor device 6 by irradiating the gas sensor device 6 with the light.

By the way, a breath sensor was experimentally manufactured as a small simple gas sensor 5 that could be used for measuring a trace chemical substance in a breath by applying the configuration as described above. As a result, a concentration of ammonia could be easily measured by monitoring a resistance value of the gas sensor 5 with a smartphone (terminal) 44 (see FIG. 38, for example).

Inside a body of an animal including a human, nitrogen is generated as ammonia when protein is decomposed inside a digestive tract. Alternatively, ammonia is generated when a microorganism and anaerobic bacteria living in a gastrointestinal tract decompose urea by using urease enzymes.

Some of the ammonia is partly absorbed into blood, and the rest is excreted as excrement to the outside. Blood containing nutrients absorbed from digestive organs is collected in a liver as a portal vein.

In the liver, nutrient substances are absorbed and also toxins are subjected to metabolism having a detoxification function.

The ammonia corresponds to the latter case and is metabolized in a cycle called a urea cycle inside the liver, and transformed into urea.

This urea is then filtered by kidneys and excreted with urine.

Furthermore, in a case where muscles are exhausted due to hard exercise, ammonia is generated in the blood and such ammonia is similarly metabolized in the urea cycle in the liver through veins, and transformed into the urea.

With such a metabolic function, the concentration of ammonia in the living body is kept at a certain level or less.

Therefore, in a case where the metabolic function in the liver has a disease and the liver function is degraded, the ammonia concentration is increased, and in a case of malnutrition state, the ammonia concentration is decreased.

However, it can be said that a living thing contains ammonia in blood as far as the living body takes nutrients and does exercise. Since ammonia is gasified by capillaries of the lungs and skin, a breath and sweat of the living thing are to contain a trace amount of ammonia.

Furthermore, alcohols such as ethanol are generated in a process of decomposing hydrocarbons, ketones such as acetone are generated in a process of decomposing sugars, and isoprene is generated in a process of decomposing cholesterol. Furthermore, in a case of a disease such as cancer or the like, various kinds of volatile organic compounds (VOCs) are generated by oxidative stress in an affected area, and are gasified in the lungs and the skin through the blood.

See, for example, "Ammonia Metabolism During Exercise" by Shohei ONISHI, and Hajime YAMAZAKI in the Bulletin of Keio University Health Center, Vol. 8, No. 1, 1989.

Therefore, it may be possible to easily measure the concentration of ammonia by applying the above-described configuration and implementing the breath sensor (gas sensor) 5.

Furthermore, fluctuations in breath components caused by lifestyle habits may be continuously examined without distress like blood sampling and the like.

Furthermore, a breath-print sensor applying the configuration as described above is mounted on, for example, a smart device or a wearable device so as to form a tool by which the above-mentioned gases may be continuously analyzed with convenience like a thermometer.

Furthermore, the present technology is useful as a screening tool for purposes of improvement of lifestyle habits and early detection of diseases.

Note that the present embodiment is not limited to the configurations described in the embodiment and each modified example described above, and various modifications can be made within a range not departing from the spirit of the present embodiment.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:
1. A gas sensor comprising:
a gas sensor cartridge; and
a gas sensor body to which the gas sensor cartridge is detachably attached, the gas sensor cartridge includes:
a case that has an intake port and an exhaust port and serves as a gas sensor chamber;
a gas sensor device provided inside the case;

an external connection terminal provided at the case and connected to the gas sensor device;

a first sealing member that seals the intake port such that the intake port is opened when the gas sensor cartridge is attached to the gas sensor body; and a second sealing member that seals the exhaust port such that the exhaust port is opened when the gas sensor cartridge is attached to the gas sensor body, an optical window is provided in the case and on a side opposite to a side of the case provided with the gas sensor device, and the gas sensor further includes a condenser lens or an optical waveguide member provided on an inner surface of the optical window or between the optical window and the gas sensor device.

2. The gas sensor according to claim 1, wherein the first sealing member is a first movable valve capable of opening and closing the intake port or a first protective film that is broken when the gas sensor cartridge is attached to the gas sensor body, and the second sealing member is a second movable valve capable of opening and closing the exhaust port or a second protective film that is broken when the gas sensor cartridge is attached to the gas sensor body.

3. The gas sensor according to claim 1, wherein the optical window has a property of transmitting light including ultraviolet (UV).

4. The gas sensor according to claim 1, wherein the optical window is provided on a side portion orthogonal to a bottom portion of the case provided with the gas sensor device, and the gas sensor further includes a reflection mirror that reflects light incident from the optical window toward the gas sensor device on a side opposite to a side of the case provided with the gas sensor device.

5. The gas sensor according to claim 1, further comprising a light source provided in the gas sensor body or a light source provided outside the optical window.

6. The gas sensor according to claim 1, wherein the light source is provided on a side portion orthogonal to a bottom portion of the case provided with the gas sensor device, and the gas sensor further includes a reflection mirror that reflects light from the light source toward the gas sensor device on a side opposite to a side of the case provided with the gas sensor device.

7. The gas sensor according to claim 1, further comprising a gas adsorption member provided inside the case.

8. The gas sensor according to claim 1, wherein the gas sensor device includes at least one of: a gas sensitive material including oxide containing Sn, W, Zn, or In or any combination of Sn, W, Zn, and In as a main material; a gas sensitive material including a semiconductor containing C as a main material; or a gas sensitive material including a halogen compound or oxide containing Cu or Ag as a main material.

9. The gas sensor according to claim 1, further comprising a non-volatile memory element provided in the case, connected to the external connection terminal, and having characteristics of the gas sensor device recorded inside.

10. The gas sensor according to claim 1, wherein the optical window is provided on a side of the case provided with the gas sensor device, and the gas sensor further includes a reflection mirror that reflects light incident from the optical window toward the gas sensor device on a side opposite to the side of the case provided with the gas sensor device.

11. The gas sensor according to claim 10, further comprising a condenser lens or an optical waveguide member provided on an optical path from the optical window to the gas sensor device.

12. The gas sensor according to claim 1, wherein the light source is provided on a side opposite to a side of the case provided with the gas sensor device.

13. The gas sensor according to claim 12, further comprising a condenser lens or an optical waveguide member provided between the light source and the gas sensor device.

14. The gas sensor according to claim 1, wherein the light source is provided on a side of the case provided with the gas sensor device, and the gas sensor further includes a reflection mirror that reflects light from the light source toward the gas sensor device on the side opposite to the side of the case provided with the gas sensor device.

15. The gas sensor according to claim 14, further comprising a condenser lens or an optical waveguide member provided on an optical path from the light source to the gas sensor device.

* * * * *